US008778410B2

(12) United States Patent
Higashiguchi et al.

(10) Patent No.: US 8,778,410 B2
(45) Date of Patent: Jul. 15, 2014

(54) ORAL OR ENTERAL COMPOSITION USEFUL FOR RECOVERY OF PHYSICAL FUNCTIONS

(75) Inventors: Takashi Higashiguchi, Suzuka (JP); Takako Hatakeyama, Nagoya (JP)

(73) Assignees: Earnest Medicine Co., Ltd., Nagoya-Shi (JP); Otsuka Pharmaceutical Factory, Inc., Naruto-Shi (JP)

(*) Notice: Subject to any disclaimer, the term of this patent is extended or adjusted under 35 U.S.C. 154(b) by 193 days.

(21) Appl. No.: 12/918,435

(22) PCT Filed: Feb. 19, 2009

(86) PCT No.: PCT/JP2009/052928
§ 371 (c)(1),
(2), (4) Date: Aug. 19, 2010

(87) PCT Pub. No.: WO2009/104696
PCT Pub. Date: Aug. 27, 2009

(65) Prior Publication Data
US 2010/0330197 A1    Dec. 30, 2010

(30) Foreign Application Priority Data

Feb. 19, 2008   (JP) ................ 2008-037113
Sep. 8, 2008    (JP) ................ 2008-230217
Oct. 16, 2008   (JP) ................ 2008-267878

(51) Int. Cl.
| A61K 31/122 | (2006.01) |
| A61K 31/194 | (2006.01) |
| A61K 31/198 | (2006.01) |
| A61K 31/205 | (2006.01) |
| A61K 31/315 | (2006.01) |
| A61K 33/30 | (2006.01) |
| A61K 33/34 | (2006.01) |
| A61P 3/02 | (2006.01) |
| A61P 35/00 | (2006.01) |

(52) U.S. Cl.
USPC ........... 424/643; 424/641; 514/494; 514/556; 514/561; 514/574; 514/690

(58) Field of Classification Search
USPC .......... 514/494, 556, 561, 574, 690; 424/641, 424/643
See application file for complete search history.

(56) References Cited

U.S. PATENT DOCUMENTS

| 4,599,232 A * | 7/1986 | Bertelli ................. 424/94.1 |
| 5,108,767 A | 4/1992 | Mulchandani et al. |
| 5,444,054 A | 8/1995 | Garleb et al. |
| 5,700,782 A | 12/1997 | Cope et al. |
| 5,719,134 A | 2/1998 | Schmidl et al. |
| 6,420,342 B1 | 7/2002 | Hageman et al. |
| 6,548,483 B2 | 4/2003 | Hageman et al. |
| 6,864,242 B2 | 3/2005 | Ernest |
| 7,196,065 B2 | 3/2007 | Ernest |
| 2002/0183263 A1 | 12/2002 | Hageman et al. |
| 2004/0067224 A1 | 4/2004 | Ernest |
| 2005/0070498 A1 | 3/2005 | Ernest |
| 2005/0276839 A1 | 12/2005 | Rifkin |
| 2008/0131561 A1 | 6/2008 | Patanawongyuneyong |
| 2008/0160086 A1 * | 7/2008 | Farber ....................... 424/488 |

FOREIGN PATENT DOCUMENTS

| JP | 60-49764 A | 3/1985 |
| JP | 61-19458 A | 1/1986 |
| JP | 7-330584 A | 12/1995 |
| JP | 2001-354553 A | 12/2001 |
| JP | 2004-81010 A | 3/2004 |
| JP | 2004-210639 A | 7/2004 |
| JP | 2005-053923 A | 3/2005 |
| JP | 2005-097161 A | 4/2005 |
| JP | 2005-336176 A | 12/2005 |
| JP | 2006-016358 A | 1/2006 |
| JP | 2008-063277 A | 3/2008 |
| JP | 2008-143811 A | 6/2008 |
| JP | 2008-255033 A | 10/2008 |
| JP | 2008-273938 A | 11/2008 |
| WO | 97/39749 A2 | 10/1997 |
| WO | 99/01044 A1 | 1/1999 |
| WO | 01/85178 A1 | 11/2001 |
| WO | 02/069964 A1 | 9/2002 |
| WO | 2007/145239 A1 | 12/2007 |

OTHER PUBLICATIONS

Merriam Webster's Collegiate Dictionary, 10th edition, Merriam-Webster, Inc.: Springfield, MA, 1996, pp. 30 (definition of alleviate) and pp. 1258 (definition of treat).*
Machine translation of IDS reference JP 2005-053923 obtained online at dossier2.ipdl.inpit.go.jp/JP/application/P/2004-300880/DOCLIST.htm:JE on Aug. 6, 2012.*
International Search Report of PCT/JP2009/052928, date of mailing May 19, 2009.
Extended European Search Report dated Jun. 10, 2013, issued in corresponding European Patent Application No. 09711926.7.
Groblewska et al., "Serum interleukin 6 (IL-6) and C-reactive protein (CRP) levels in colorectal adenoma and cancer patients", Clin Chem Lab Med 2008; 46(10), pp. 1423-1428, Bialystok, Poland.
Koike et al., "Preoperative C-Reactive Protein as a Prognostic and Therapeutic Marker for Colorectal Cancer", Journal of Surgical Oncology, 2008; 98, pp. 540-544, Mie, Japan.

(Continued)

*Primary Examiner* — John Pak
(74) *Attorney, Agent, or Firm* — Westerman, Hattori, Daniels & Adrian, LLP

(57) ABSTRACT

The present invention provides an oral or enteral composition incorporating not only BCAA but other nutrients to be conducive to comprehensive recovery from fatigue, and improvement in total physical condition.

The oral or enteral composition is formulated as a composite of a branched-chain amino acid, coenzyme $Q_{10}$, L-carnitine, a citric acid, and zinc.

18 Claims, 14 Drawing Sheets

(56) References Cited

OTHER PUBLICATIONS

Wilop et al., "Correlation of C-Reactive Protein with Survival and Radiographic Response to First-Line Platinum-Based Chemotherapy in Advanced Non-Small Cell Lung Cancer", ONKOLOGIE, 2008; 31, pp. 665-670, Germany.

Kasprzyk et al., "Assessment of acute phase proteins as prognostic factors in patients surgically treated for non-small cell lung cancer", Polish Pneumonology and Allergology, 2008; vol. 76, No. 5, pp. 321-326, Poznan, Poland.

Nozoe et al., "Preoperative Elevation of Serum C-Reactive Protein as an Independent Prognostic Indicator of Colorectal Carcinoma", Surg Today, 2008; 38, pp. 597-602, Japan.

* cited by examiner

ORAL OR ENTERAL COMPOSITION USEFUL FOR RECOVERY OF PHYSICAL FUNCTIONS

TECHNICAL FIELD

The present invention relates to an oral or enteral composition conducive to efficient body energy production, while preventing degradation of muscle protein and facilitating synthesis of muscle protein. More specifically, the present invention relates to an oral or enteral composition containing a branched-chain amino acid (BCAA), coenzyme $Q_{10}$, L-carnitine, a citric acid and zinc. The present invention particularly relates to an oral or enteral composition useful as a nutrient for use in muscular training for early ambulation of elderly people or rehabilitation patients. The present invention further relates to an oral or enteral composition conducive to early recovery from cancer therapies including operations, chemotherapies and radial ray therapies, or biological invasion caused by injury, infectious diseases or various organopathies; alleviation of the symptoms and pathosis of terminal stage cancers; early recovery of rehabilitation patients (including elderly people and dysphagia patients); and reduction of hospitalization period.

BACKGROUND ART

Valine, leucine, and isoleucine, among the nine essential amino acids that cannot be synthesized in the human body, are categorized as branched-chain amino acids because they all have branched-chain structures. Unlike the other amino acids that are metabolized mainly in the liver, BCAA is metabolized in muscles. Further, BCAA is the only essential amino acid serving as a muscle energy source. Therefore, recently, there have been attempts to incorporate BCAA into dietary supplements or beverages.

For example, Patent Literature 1 discloses a food composition containing 30% or more of at least one of valine, leucine and isoleucine; 10% or more of arginine; and 30% or more of protein. Patent Literature 1 alleges that this food composition has an effect of enhancing functions of muscular movements during sports or physical labor.

Further, Patent Literature 2 discloses a supplement drink effective for physical fatigue that contains D-ribose and a magnesium salt and/or a branched-chain amino acid.

Further, Patent Literature 3 discloses that a composition containing pantethine and a branched-chain amino acid significantly decreases the blood lactic acid level after physical exercise. Accordingly, Patent Literature 3 provides a composition for reducing fatigue or malaise.

CITATION LIST

[Patent Literature 1] Japanese Examined Patent Publication No. 1991-68665
[Patent Literature 2] Japanese Unexamined Patent Publication No. 2005-336176
[Patent Literature 3] Japanese Unexamined Patent Publication No. 2006-16358

SUMMARY OF INVENTION

Technical Problem

The aforementioned composition containing BCAA can reduce physical fatigue caused by exercise. Therefore, it is useful for healthy people, particularly for sports athletes.

However, for the patients subjected to various medical treatments involving biological invasion such as operation, chemotherapies, radiation treatments; the patients of diseases involving biological invasion such as malignant tumors, injury, infectious diseases etc.; and malnourished valetudinarians, recuperating patients or the like, for example, elderly people with decreased strength, particularly for elderly people hospitalized for operations or treating bone fracture, who are under vocational rehabilitation, ensuring early recovery of organs from biological invasion and reduction in physical fatigue caused by rehabilitation is not sufficiently helpful to facilitate their quick recovery from fatigue. For these patients, improvement in their general physical condition in consideration of other fatigue factors, such as stress, is significantly important for early recovery or early release from hospitals, and such importance has gained public recognition.

This recognition presumably comes from a recent trend in which people are aware of complex causes of fatigue. In fact, the causes of fatigue are variable; for example, in addition to lactates, phosphates are also now attracting attention as a cause of fatigue.

Under such circumstances, there has been a strong demand from medical personnel and other relevant parties for oral or enteral compositions incorporating nutrients other than BCAA, which are effective for comprehensive recovery from fatigue, functional recovery or improvement of tissues, and improvement in total physical condition; the compositions; oral or enteral compositions having a new formulation enabling elderly people or patients having dysphagia to more easily take the composition; and oral or enteral compositions that can be processed into various forms, such as drinks, while ensuring the same effect.

Cancer is a leading cause of death in Japan. According to an estimation by a research group from the nation's Ministry of Health, Labour and Welfare, one out of two males and one out of three females will have cancer at some point in their lifetime. In recent years, various cancer therapies have been studied and used for treatments; therefore, treatment results are improving steadily. Nevertheless, there are still potential risks for cancers to develop to a terminal stage due to retardation of discovery, metastasis, relapse, etc. Since terminal cancers involve severe physical pains including algia, malaise, dyspnea and insomnia, the terminal care must focus on reduction of these symptoms to improve the Quality of Life (QOL) of the terminal cancer patients. Therefore, there also has been a strong need for oral or enteral compositions effective for alleviating various symptoms of terminal cancer.

Solution to Problem

The inventors of the present invention conducted intensive studies to solve the above problems, and found that the above problems can be solved using an oral or enteral composition containing coenzyme $Q_{10}$, L-carnitine, a citric acid and zinc in addition to BCAA. More specifically, an oral or enteral composition combining BCAA, coenzyme $Q_{10}$, L-carnitine, a citric acid and zinc significantly facilitates recovery of bodily function, thereby achieving early recovery in the patients of various diseases, or in recuperating patients. The inventors also found that the oral or enteral composition has an antitumor effect, and an effect of alleviating the symptoms, such as algia, malaise, dyspnea and insomnia, of terminal cancers. Based on these findings, the inventors conducted further research, and completed the present invention.

Specifically, the present invention provides the following embodiments.

Item 1. An oral or enteral composition comprising a branched-chain amino acid, coenzyme $Q_{10}$, L-carnitine, a citric acid, and zinc.

Item 2. The oral or enteral composition according to Item 1, wherein the oral or enteral composition is in a form of gel.

Item 3. The oral or enteral composition according to Item 1, wherein the oral or enteral composition is in a form of gel, and
the composition comprises 0.71 to 7.14 wt. % of a branched-chain amino acid, 0.007 to 0.086 wt. % of coenzyme $Q_{10}$, 0.0035 to 0.72 wt. % of L-carnitine, 0.071 to 2.144 wt. % of a citric acid, and 0.0005 to 0.016 wt. % of zinc, based on the total amount of the composition.

Item 4. The oral or enteral composition according to Item 1, wherein the oral or enteral composition is in a form of gel, and
the composition comprises 0.8 to 5.0 wt. % of a branched-chain amino acid, 0.01 to 0.07 wt. % of coenzyme $Q_{10}$, 0.005 to 0.3 wt. % of L-carnitine, 0.08 to 1.8 wt. % of a citric acid, and 0.0008 to 0.008 wt. % of zinc, based on the total amount of the composition.

Item 5. The oral or enteral composition according to Item 1, wherein the oral or enteral composition is in a form of gel, and
the composition comprises 1.0 to 3.0 wt. % of a branched-chain amino acid, 0.015 to 0.05 wt. % of coenzyme $Q_{10}$, 0.01 to 0.07 wt. % of L-carnitine, 0.1 to 1.5 wt. % of a citric acid, and 0.001 to 0.0035 wt. % of zinc, based on the total amount of the composition.

Item 6. The oral or enteral composition according to Item 1, wherein the oral or enteral composition is in a form of gel, and
the composition comprises 1.5 to 2.5 wt. % of a branched-chain amino acid, 0.018 to 0.03 wt. % of coenzyme $Q_{10}$, 0.03 to 0.05 wt. % of L-carnitine, 0.6 to 1.0 wt. % of a citric acid, and 0.002 to 0.0028 wt. % of zinc, based on the total amount of the composition.

Item 7. The oral or enteral composition according to Item 1, wherein the branched-chain amino acid comprises valine, leucine and isoleucine at a weight ratio of 1:0.8 to 2.5:0.7 to 2.2.

Item 8. The oral or enteral composition according to Item 1, wherein the oral or enteral composition further comprises 8 to 12 parts by weight of copper, per 100 parts by weight of zinc.

Item 9. The oral or enteral composition according to Item 1, wherein the oral or enteral composition is in a form of gel, and
the composition comprises 60 to 90 wt. % of water and 0.5 to 1.5 wt. % of a gelatinizer based on the total amount of the composition.

Item 10. The oral or enteral composition according to Item 1, wherein the oral or enteral composition has a viscosity in a range of from 500 to 20,000 mPa·s at 25° C.

Item 11. The oral or enteral composition according to Item 1, wherein the oral or enteral composition is a nutrient.

Item 12. The oral or enteral composition according to Item 11, wherein the oral or enteral composition is a food for a cancer patient.

Item 13. The oral or enteral composition according to Item 11, wherein the oral or enteral composition is a food for alleviating a symptom or improving nutritive condition of a cancer patient.

Item 14. The oral or enteral composition according to Item 11, wherein the cancer patient is a terminal cancer patient.

Item 15. The oral or enteral composition according to Item 1, wherein the oral or enteral composition is a medical composition.

Item 16. The oral or enteral composition according to Item 15, wherein the oral or enteral composition is used for alleviating or treating cancers.

Item 17. The oral or enteral composition according to Item 16, wherein the oral or enteral composition is used for alleviating or treating terminal cancers.

Item 18. The oral or enteral composition according to Item 16, wherein the oral or enteral composition is used for alleviating a symptom of terminal cancer.

Item 19. The oral or enteral composition according to Item 18, wherein the symptom of terminal cancer is at least one selected from the group consisting of algia, malaise, dyspnea, insomnia, and constipation.

Item 20. An agent for reducing fatigue comprising the oral or enteral composition according to Item 1.

Item 21. An agent for suppressing lactic acid production in a living body comprising the oral or enteral composition according to Item 1.

Item 22. An anticancer agent comprising the oral or enteral composition according to Item 1.

Item 23. An agent for relieving pains of terminal cancer patients comprising the oral or enteral composition according to Item 1.

Item 24. An agent for alleviating symptoms of cancer patients and improving their nutritional conditions comprising the oral or enteral composition according to Item 1.

Item 25. A method for treating or alleviating a cancer, comprising administering an oral or enteral composition, which comprises a branched-chain amino acid, coenzyme $Q_{10}$, L-carnitine, a citric acid, and zinc, to a cancer patient.

Item 26. The method according to Item 25, wherein the method treats or alleviates a terminal cancer.

Item 27. The method according to Item 25, wherein the method alleviates symptoms of a terminal cancer.

Item 28. The method according to Item 27, wherein the symptoms include at least one selected from the group consisting of algia, malaise, dyspnea, insomnia, and constipation.

Item 29. Use of an oral or enteral composition comprising a branched-chain amino acid, coenzyme $Q_{10}$, L-carnitine, a citric acid, and zinc for production of an agent for treating or alleviating cancers.

Item 30. The use according to Item 29, wherein the use is for production of an agent for treating or alleviating terminal cancers.

Item 31. The use according to Item 29, wherein the agent for treating or alleviating cancers are an agent for alleviating symptoms of terminal cancers.

Item 32. The use according to Item 31, wherein the symptoms include at least one selected from the group consisting of algia, malaise, dyspnea, insomnia, and constipation.

Advantageous Effects of Invention

The composition of the present invention is conducive to muscular strength enhancement due to efficient energy production and improved anabolic action; and to quick recovery from muscle fatigue due to reduction in oxidative stress and elimination of fatigue products (lactic acid, etc). Therefore, the composition of the present invention is useful as a nutritional supplement or medicine for healthy people to recover from various types of fatigue caused by work, sports etc., as well as for valetudinarians and recuperating patients. The composition of the present invention is particularly useful as a medicine for elderly people and rehabilitants, who are subjected to muscle training to quickly recover from their illnesses.

More specifically, the nutritive conditions of elderly people, valetudinarians etc. can be improved in a short period by taking the composition of the present invention, which ensures a stable supply of required nutrition and energy.

The composition of the present invention is also advantageous in that, by forming the composition of the present invention into a gel using a gelatinizer, even stroke patients and patients having difficulty in the intake or deglutition of food or drink can take the composition safely and efficiently.

In the composition of the present invention, the components interactively function to facilitate efficient energy production and increase metabolic turnover of energy, thereby eliminating physical fatigue. The composition of the present invention also reduces consumption of muscle protein due to energy production, thereby suppressing muscular depression, and thereby maintaining bodily function. Moreover, the composition of the present invention is conducive to early recovery or functional improvement of healthy tissues damaged by biological invasion of the primary diseases and the therapies. Accordingly, the composition of the present invention has an assumed effect for protein energy malnutrition (PEM) or cachexia of cancer patients; medical biological invasion such as cancer treatments; or debilitating illness such as cachexia of chronic obstructive lung disease (COPD), injury, infectious diseases or the like.

As described, the composition of the present invention facilitates recovery of bodily function, and is useful for treating or alleviating various diseases. In particular, with its excellent antitumor effect, the composition of the present invention is useful as a medicine for treating or alleviating cancers. Moreover, the composition of the present invention has an excellent effect of alleviating the symptoms, such as algia, malaise, dyspnea, insomnia etc., of terminal cancers. Therefore, the composition of the present invention is useful for alleviating pains of terminal cancer patients and improving their QOL.

BEST MODE FOR CARRYING OUT THE INVENTION

I. Oral or Enteral Composition

The composition of the present invention is more specifically described below.

A. Ingredients of Oral or Enteral Composition

The composition of the present invention is characterized by comprising BCAA, coenzyme $Q_{10}$, L-carnitine, a citric acid and zinc, as essential ingredients.

(1) BCAA

As described above, BCAA stands for branched-chain amino acid. The three amino acids valine, leucine, and isoleucine are represented by the following equations.

[Chem. 1]

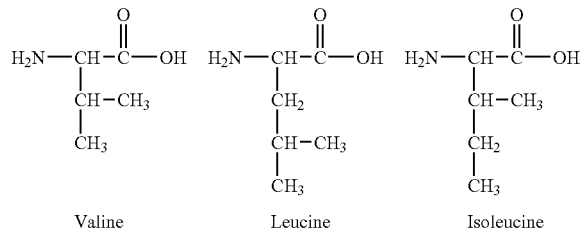

Valine　　　Leucine　　　Isoleucine

The following explains the function of BCAA as a nutrient of the composition of the present invention.

(i) BCAA accounts for about 20% of the proteins for constructing muscles. This corresponds to about 30 to 40% of the essential amino acids contained in muscle proteins. BCAA is a material of muscles, serving as a main amino acid for constructing muscles.

(ii) BCAA is metabolized in muscles to be used as a major energy source of muscles.

(iii) During exercise, although BCAA in muscles burns to generate energy, muscular degradation and damage occur at the same time. BCAA supplied before or during exercise is efficiently consumed as energy, and suppresses muscular degradation and damage. In particular, leucine facilitates synthesis of muscle protein.

(iv) When intensive exercise is continued, lactic acid is increased as the metabolite of energy consumption. This causes the pH value of the muscles to be shifted from neutral to acidic, decreasing ATP activity (contraction energy). This hinders smooth muscle contraction, hampering continuous exercise. BCAA has a property of suppressing the generation of lactic acid, i.e., one of the causes of muscle fatigue.

(v) BCAA relieves central fatigue by blocking tryptophan from entering the brain, thereby preventing an increase of serotonin, which is a neurotransmission substance and one of the causes of tiredness, in the brain.

(vi) Moreover, it is reported that BCAA acts on the process of changing acetyl-CoA into a citric acid as a result of fat metabolism. Thus, BCAA plays an important role when fat enters into a citric acid cycle, and helps smooth circulation of the citric acid cycle, thereby facilitating bodily energy production.

In the present invention, BCAA may be selected from valine, leucine and isoleucine. These BCAA can be used solely or in combination. The BCAA used in the present invention is preferably a combination of three BCAAs, i.e., valine, leucine and isoleucine.

The weight ratio of valine, leucine, and isoleucine contained in various foods such as fish, egg, milk etc., or those contained in mother's milk is about 1:2:1.

However, in the present invention, the weight ratio of valine, leucine and isoleucine is 1:0.8 to 2.5:0.7 to 2.2, more preferably 1:1 to 2.2:1 to 1.9.

The proportion of BCAA in the composition of the present invention varies depending on the form, usage etc. of the composition. The proportion of BCAA is preferably in a range of from 0.65 to 7 wt. %, more preferably 1.2 to 5 wt. %, based on the total amount of the composition. When the composition of the present invention is a gel, the proportion of BCAA is preferably in a range of from 0.71 to 7.14 wt. %, more preferably 0.71 to 3.57 wt. %, further preferably 1.42 to 2.86 wt. %. The particularly preferred BCAA proportion of the composition of the present invention in a gel form is in a range of from 0.8 to 5.0 wt. %, more preferably 1.0 to 3.0 wt. %, particularly preferably 1.5 to 2.5 wt. %.

(2) Coenzyme $Q_{10}$

Coenzyme $Q_{10}$ is expressed by the following equation (I):

[Chem. 2]

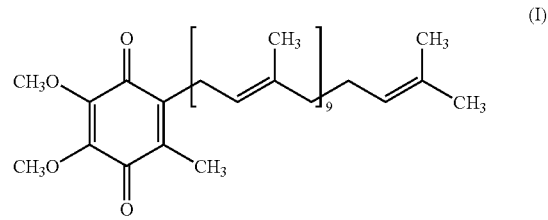

The general name of coenzyme $Q_{10}$ is ubidecarenone (molecular formula: $C_{59}H_{90}O_4$, molecular weight=863.36). Coenzyme $Q_{10}$ is known to be hardly water soluble, though it is highly soluble in ether or the like. Coenzyme $Q_{10}$ is also known as a substance which decomposes by light, generating hydroquinone, ubichromenol etc. $CoQ_{10}$ has a bioactivity as a coenzyme (involved in 95% of synthesis of the energy source ATP), and also has a function similar to vitamins, i.e., the property of increasing oxygen utilization efficiency. $CoQ_{10}$ also serves as a metabolic cardiac stimulant, and is reported to have a pharmacological effect of alleviating mild to moderate congestive heart disorders.

$CoQ_{10}$ is also reported to increase stamina. Intake of $CoQ_{10}$ facilitates energy production, and thereby allows for an increase in stamina and extension of exercise time. $CoQ_{10}$ is also known to facilitate recovery from fatigue due to exercise.

The $CoQ_{10}$ level is easily decreased by aging. Additionally, to relieve or prevent the symptoms of various heart diseases often seen in elderly people, such as ischemic heart disease, it is effective to take $CoQ_{10}$ as a nutrient. Although $CoQ_{10}$ is generally contained in fishes, meats, or seaweeds, only a few natural foods contain a high amount of $CoQ_{10}$. Therefore, it is difficult to take $CoQ_{10}$ from natural foods during usual meals in an amount sufficient to compensate for the shortage.

$CoQ_{10}$ is a lipophilic solid having a low melting point. Because of its poor water solubility, $CoQ_{10}$ is known for its low absorptivity in oral administration. To take $CoQ_{10}$ as a nutrient, it is necessary to improve the absorptivity and prevent crystallization, sedimentation by coagulation or the like. Further, in consideration of oral administration, it is important to ensure the safety thereof.

Since $CoQ_{10}$ has poor water solubility, it is generally dissolved in hydrophilic organic solvents such as vegetable oil or animal oil. Otherwise, $CoQ_{10}$ is used by being dispersed or emulsified in an aqueous solution using an emulsifier, dispersant, surfactant or the like.

However, since the composition of the present invention uses water-soluble $CoQ_{10}$, the $CoQ_{10}$ exhibits excellent dispersibility in the composition, and coagulation or sedimentation does not easily occur. In particular, water soluble $CoQ_{10}$ is highly absorbable in a living body. Examples of water-soluble $CoQ_{10}$ are disclosed, for example, in Japanese Unexamined Patent Publication No. 2004-196781, Japanese Unexamined Patent Publication No. 2003-55203, and Japanese Unexamined Patent Publication No. 2003-238396. Further, water-soluble $CoQ_{10}$ is commercially available (product name: Aqua Q10L10 (Nisshin Pharma Inc.)).

In the composition of the present invention, the ratio of $CoQ_{10}$ is, for example, 0.1 to 12 parts by weight, preferably 0.2 to 3 parts by weight, particularly preferably 1 to 1.4 parts by weight, per 100 parts by weight of BCAA contained in the composition.

Further, although the proportion of $CoQ_{10}$ in the composition of the present invention varies depending on the above-specified compounding ratio of $CoQ_{10}$, or the form and usage of the composition, the proportion of $CoQ_{10}$ is preferably 0.005 to 0.5 wt. %, particularly preferably 0.01 to 0.05 wt. %, based on the total amount of the composition. When the composition of the present invention is a gel, the proportion of $CoQ_{10}$ is preferably 0.007 to 0.085 wt. %, more preferably 0.007 to 0.043 wt. %, particularly preferably 0.014 to 0.029 wt. %. The particularly preferred $CoQ_{10}$ proportion of the composition of the present invention in a gel form is in a range of from 0.01 to 0.007 wt. %, more preferably 0.015 to 0.05 wt. %, particularly preferably 0.018 to 0.03 wt. %. In the composition of the present invention, the proportion of $CoQ_{10}$ is higher than the existing products. This high proportion of $CoQ_{10}$ is further mixed with other essential ingredients, thereby exhibiting the above-mentioned effects advantageously.

(3) L-carnitine

L-carnitine (C7H15NO3; molecular weight=161.20) is produced in liver and kidney from the essential amino acids methionine and lysine. L-carnitine has the following structure.

[Chem. 3]

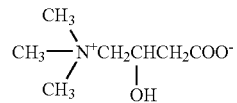

L-carnitine is required in the process of burning fatty acids to produce energy. More specifically, the fatty acids are intracellularly metabolized by mitochondria, and carnitine serves to transfer fatty acids into mitochondria.

As such, L-carnitine is important for body energy production. Another reported function of L-carnitine is facilitation of recovery from muscle fatigue.

Although L-carnitine is synthesized within the body, the body loses L-carnitine synthesis ability with aging, therefore making it important to take supplementary L-carnitine from outside the body.

In the composition of the present invention, the ratio of L-carnitine is, for example, 1 to 50 parts by weight, preferably 1.5 to 20 parts by weight, more preferably 1.8 to 5 parts by weight, per 100 parts by weight of BCAA contained in the composition. In the composition of the present invention, the ratio of L-carnitine to BCAA is important; if the ratio falls below the above range, the above-mentioned effects of the present invention are likely to be impaired.

Further, in the composition of the present invention, although the proportion of L-carnitine varies depending on the above-specified ratio of L-carnitine, or the form and usage of the composition, the proportion of L-carnitine is preferably in a range of from 0.003 to 0.7 wt. %, more preferably 0.003 to 0.4 wt. %, particularly preferably 0.008 to 0.15 wt. %, based on the total amount of the composition. When the composition of the present invention is a gel, the proportion of L-carnitine is 0.0035 to 0.72 wt. %, preferably 0.0035 to 0.36 wt. %, more preferably 0.009 to 0.143 wt. %, particularly preferably 0.01 to 0.1 wt. %. The particularly preferred L-carnitine proportion in the composition of the present invention in a gel form is in a range of from 0.005 to 0.3 wt. %, more preferably 0.01 to 0.07 wt. %, particularly preferably 0.03 to 0.05 wt. %.

(4) Citric Acid

Citric acids have the following structure. Citric acids are contained in a wide range of plants in free form or as salts. Citric acids are particularly known as a major component of the sour taste of citrus fruits, such as lemon, grapefruit, etc.

[Chem. 4]

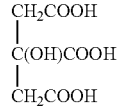

Citric acids play a predominant role in energy metabolism, as the intermediate of sugar metabolism (citric acid cycle).

Muscle fatigue causes a lack of oxygen, thereby causing lactic acid to accumulate. Since lactic acid hinders blood circulation, blood circulation is more constricted. This creates a vicious cycle.

Citric acids undergo chelate bonding with calcium ions. This suppresses the coagulation of platelets, improves the deformability of erythrocytes, and suppresses the adhesion of leucocytes, thereby increasing blood circulation. As such, citric acids provide an effect of preventing and alleviating fatigue.

In the present invention, citric acids may have free forms, or may be in the form of salts. Examples of citric acid salts include alkali metal salts such as sodium salt, or potassium salt.

In the composition of the present invention, the ratio of the citric acid is, for example, 20 to 150 parts by weight, preferably 30 to 50 parts by weight, per 100 parts by weight of BCAA contained in the composition. In the composition of the present invention, the ratio of citric acid to BCAA is important; if the ratio exceeds the above range, the above-mentioned effects of the present invention are likely to be impaired.

The proportion of citric acid in the composition of the present invention varies depending on the above-mentioned ratio of the citric acid and the form and usage of the composition. The proportion of citric acid is preferably in a range of from 0.06 to 2.4 wt. %, particularly preferably 0.3 to 2 wt. %, based on the total amount of the composition. When the composition of the present invention is a gel, the proportion of citric acid is 0.071 to 2.144 wt. %, preferably 0.071 to 1.072 wt. %, more preferably 0.35 to 0.86 wt. %. The particularly preferred citric acid proportion in the composition of the present invention in a gel form is in a range of from 0.08 to 1.8 wt. %, more preferably 0.1 to 1.5 wt. %, particularly preferably 0.6 to 1.0 wt. %.

The ratio and proportion of citric acid specified above are calculated based on the amount of a free citric acid.

(5) Zinc

Zinc can serve as the central metal of various enzymes, such as an enzyme involved in the metabolism in protein synthesis or degradation. Zinc is presumably conducive to the above-mentioned effect of the present invention. In the present invention, zinc is in the form of organic salt, inorganic salt, or mineral salt.

In the composition of the present invention, the ratio of zinc is, for example, 0.012 to 1.2 parts by weight, preferably 0.065 to 0.25 parts by weight, per 100 parts by weight of BCAA contained in the composition.

The proportion of zinc of the composition of the present invention varies depending on the above-mentioned ratio of zinc, and the form and usage of the composition. However, the proportion of zinc is preferably 0.0002 to 1.2 wt. %, particularly preferably 0.0005 to 0.25 wt. %, based on the total amount of the composition. When the composition of the present invention is a gel, the proportion of zinc is preferably 0.0005 to 0.016 wt. %, more preferably 0.0005 to 0.008 wt. %, particularly preferably 0.001 to 0.004 wt. %. The particularly preferred zinc proportion in the composition of the present invention in a gel form is in a range of from 0.0008 to 0.008 wt. %, more preferably 0.001 to 0.0035 wt. %, particularly preferably 0.002 to 0.0028 wt. %.

(6) Mineral

As required, the composition of the present invention may contain minerals other than zinc, in addition to the essential ingredients (1) to (5). The incorporation of minerals is effective to enhance the effect of facilitating recovery of bodily function, particularly to enhance the antitumor effect or the effect of alleviating the symptoms, such as insomnia, of terminal cancer.

The minerals contained therein are not limited insofar as they are food-hygienically acceptable. Examples of the minerals include copper, calcium, iron, sodium, potassium, phosphorus, and magnesium. These minerals may be used solely or in combination. Among them, copper is particularly preferable because it is a constituent of hemoglobin. The minerals are contained in the form of organic salt, inorganic salt, or mineral salt.

In particular, in terms of enhancing the antitumor effect or the effect of alleviating the symptoms, such as insomnia, of terminal cancer, it is preferable to contain copper as an additional mineral to zinc. When containing copper together with zinc, their ratio (weight ratio) is not particularly limited. For example, 8 to 120 parts by weight, preferably 10 parts by weight, of copper is contained per 100 parts by weight of zinc.

(7) Water and Gelatinizer

To form the composition of the present invention into a liquid composition, a gel composition or a semisolid composition, water is added in addition to the above ingredients. The water incorporated in the composition of the present invention is not limited insofar as it is pharmaceutically acceptable; an example thereof is purified water. The proportion of water is, for example, 60 to 90 wt. %, preferably 70 to 85 wt. %, based on the total amount of the composition.

To form the composition of the present invention into a liquid composition or a gel composition, water is added in addition to the above ingredients. The water incorporated in the composition of the present invention is not limited insofar as it is pharmaceutically acceptable; an example thereof is purified water.

When the composition of the present invention is a liquid composition or a gel composition, the proportion of water is, for example, 60 to 90 wt. %, preferably 70 to 85 wt. %, based on the total amount of the composition.

To form the composition of the present invention into a gel composition (jelly), a gelatinizer is added. The gelatinizer is not particularly limited insofar as it is pharmaceutically acceptable. Examples of gelatinizers include various polysaccharides such as gellan gum, pectin, curdlan, pullulan, locust bean gum, carrageenan, xanthan gum, guar gum, carboxymethylcellulose sodium, hydroxyethylcellulose, sodium alginate, agar, gum arabic, and tragacanth.

When the composition of the present invention is a gel, the proportion of the gelatinizer is, for example, 0.05 to 1.5 wt. %, preferably 0.1 to 0.4 wt. %, based on the total amount of the composition. However, the proportion is adjusted depending on the type of gelatinizer.

(8) Other Ingredients

In addition to the above ingredients, the composition of the present invention may contain, as required, proteins, saccharides, lipids, plant fibers, vitamins, taste components or the like. The compositions and amounts of the other ingredients are appropriately determined according to the energy amount of the composition, the required quantity of each nutrient, the compounding amount of $CoQ_{10}$, or the like.

Examples of the proteins used for the composition of the present invention include animal proteins such as casein, casein salts including casein sodium and casein calcium, hen egg protein, milk protein, or meat protein; vegetable proteins such as soy protein or soy peptide; and yeast-derived proteins. These proteins may be used solely or in combination. It is also possible to use decomposition products or amino acids of these proteins.

When the composition of the present invention contains protein, the ratio of the protein is generally 0.05 to 12.8 parts by weight, preferably 0.1 to 10 parts by weight, per 100 parts by weight of BCAA contained in the composition.

Examples of saccharides used for the composition of the present invention include sugar; maltodextrin; dextrin; candy powder; monosaccharides such as glucose or fructose; disaccharides such as maltose or lactose; granulated sugar; and oligosaccharide. These saccharides may be used solely or in combination.

When the composition of the present invention contains saccharide, the ratio of the sugar is generally 12.4 to 1,240 parts by weight, preferably 60 to 250 parts by weight, per 100 parts by weight of BCAA contained in the composition. The proportion of saccharide in the composition of the present invention varies depending on the above-specified ratio of saccharide, the form of the composition or the like. The proportion of saccharide is preferably 3 to 80 wt. %, particularly preferably 6 to 60 wt. %, based on the total amount of the composition. The particularly preferred saccharide proportion in the composition of the present invention in a gel form is in a range of from 6 to 75 wt. %, preferably 12 to 50 wt. %.

Examples of dietary fibers contained in the composition of the present invention include various indigestible polysaccharides such as cellulose, lignin, resistant starch, polydextrose, oligosaccharide, and enzymatically hydrolyzed guar gum. These dietary fiber components may be used solely or in combination.

When the composition of the present invention contains a dietary fiber, the ratio of the dietary fiber is generally 3 to 10 parts by weight, preferably 1 to 20 parts by weight, per 100 parts by weight of BCAA contained in the composition. The proportion of the dietary fiber in the composition of the present invention varies depending on the above-specified ratio of fibers, the form and usage of the composition, or the like. The proportion of the dietary fiber is preferably in a range of from 0.3 to 5 wt. %, particularly preferably 0.5 to 2 wt. %, based on the total amount of the composition. The particularly preferred dietary fiber proportion in the composition of the present invention in a gel form is in a range of from 0.70 to 2.85 wt. %, preferably 0.70 to 1.50 wt. %.

Examples of vitamins contained in the composition of the present invention include various lipid-soluble or water-soluble vitamins such as vitamin A, vitamin $B_1$, vitamin $B_2$, vitamin $B_6$, vitamin $B_{12}$, vitamin C, vitamin D, vitamin K, niacin, folic acid, and pantothenic acid. These vitamins may be used solely or in combination.

Among the above vitamins, vitamin E has a superior antioxidant effect, and the vitamin B group is conducive to energy production and recovery from fatigue. It is particularly preferable to contain the vitamin B group in the composition of the present invention, in addition to the above essential ingredients (1) to (5).

When the composition of the present invention contains a vitamin, the compounding ratio of the vitamin is generally 0.1 to 2 parts by weight, preferably 0.3 to 1 parts by weight, per 100 parts by weight of BCAA contained in the composition. Further, when the composition of the present invention contains only vitamin B, the ratio of the vitamin B is preferably 0.1 to 2 parts by weight, more preferably 0.1 to 1 parts by weight, per 100 parts by weight of BCAA contained in the composition.

The proportion of vitamin in the composition of the present invention varies depending on the above-specified ratio of vitamin, the type of the vitamin, the form and usage of the composition, or the like. However, the proportion of the dietary fiber is preferably in a range of from 0.001 to 0.1 wt. %, particularly preferably 0.002 to 0.04 wt. %, based on the total amount of the composition. Further, when the composition of the present invention contains only vitamin B, the proportion of the vitamin B is preferably in a range of from 0.001 to 0.1 wt. %, particularly preferably 0.002 to 0.01 wt. %, based on the total amount of the composition. The particularly preferred vitamin proportion in the composition of the present invention in a gel form is in a range of from 0.001 to 0.05 wt. %, preferably 0.008 to 0.02 wt. %.

Further, the composition of the present invention may contain a taste component such as sodium chloride, sodium glutamate, fruit juice or the like, and flavors such as pineapple flavor, lemon flavor, orange flavor, coffee flavor, green-tea flavor, milk flavor or the like.

The composition of the present invention may further contain, in addition to the above ingredients, other pharmacological active components, binders, disintegrants, lubricants, excipients, moistening agents, buffers, preservatives, perfume and the like, depending on its form and usage.

B. Form and Usage of Oral or Enteral Composition

As long as it allows for oral or enteral administration, the composition of the present invention may be formed into gels, liquids, semisodium formulations, powder medicines, tablets, granules, capsules, syrups or the like. In particular, the gel compositions can be more safely and efficiently taken by stroke patients or patients having intake or deglutition difficulties.

When the composition of the present invention is formed into a gel composition, the viscosity is preferably in a range of from 500 to 20,000 mPa·s at 25° C., 2,000 to 20,000 mPa·s (7,000 to 11,000 mPa·s at 37° C.), more preferably 10,000 to 15,000 mPa·s at 25° C. The viscosity is much higher than that of a general jelly food. This prevents accidental ingestion or aspiration pneumonia caused by accidental inpouring into the trachea or the lung during the oral administration of the composition to elderly people or patients who often have intake or deglutition difficulties, thereby ensuring high safety. Further, the high viscosity helps to prevent reverse flow or like troubles when the composition of the present invention is administered through a tube to a patient with a gastric fistula of percutaneous endoscopic gastrostomy (PEG), and thereby allows for smooth introduction of the composition into the body. The above viscosity is measured by a B-type rotation viscosity meter (RB-80L, Toki Sangyo Co. Ltd.) using a rotor M3, at 6 rpm and 25° C.

The composition of the present invention may be used in a form of foods as a nutrient, or may be used as a medical composition in the medical field.

The composition of the present invention facilitates recovery from fatigue and suppresses lactic acid production in a living body. Moreover, the composition of the present invention is conducive to improvement in the general state of valetudinarians and convalescing patients (particularly, elderly people and rehabilitants); alleviation of protein energy malnutrition (PEM) or cachexia in cancer patients; alleviation of biological invasion such as cancer treatment or cachexia in chronic obstructive lung disease (COPD); treatment or alleviation of debilitating illness such as injury, infectious diseases or the like; treatment or alleviation of cancers; alleviation of various symptoms of terminal cancer, and the like. Among the various effects, in particular, the composition of the present invention provides excellent effects of alleviating symptoms of cancers and improving nutritive conditions of cancer patients, and is therefore useful as a nutrient or a medical composition for cancer patients. In particular, the composition of the present invention has a remarkable effect of alleviating the symptoms of terminal cancers, and is therefore useful as a nutrient or a medical composition for easing pains of terminal cancer patients and improving their QOL. Examples of said symptoms of terminal cancer include at least one of algia, malaise, dyspnea, insomnia, and constipation.

The intake or administration of the composition of the present invention is determined according to the age, condition, symptom or the like of the patient. For example, intake or administration amount of the composition of the present invention for an adult is a dose corresponding to 1,250 to 5,000 mg of BCAA; this dose of the composition is taken or administered once, or 2 to 5 times a day.

The composition of the present invention may be processed into a nutrient in the form of food, or in other forms such as gel compositions, granules, fine granules, capsules, tablets, powder, liquids, and semisodium formulations. By processing the composition of the present invention into a nutrient, the composition can be used as food for specified health use, dietary supplement, functional food, patient food or the like as well as general food products. The nutrient made of the composition of the present invention is very useful as a food for the above-mentioned purposes. In particular, the nutrient is useful as a special food for cancer patients. The nutrient is especially useful as a food that can ease the pains of terminal cancer patients and thereby improve their QOL. The intake of the nutrient is appropriately determined according to the age, condition, symptom or the like of the patient. The above dose (a dose corresponding to 1,250 to 5,000 mg of BCAA, taken or administered once, or 2 to 5 times a day) can be adopted.

When the composition of the present invention is processed into a medical composition, the medical composition is processed into an internal medicine or enteral medicine. The medical composition is used for the above usages. Among the above usages, in particular, the medical composition has a remarkably significant antitumor effect, and is therefore useful as an antitumor agent. The composition of the present invention also has an outstanding effect of alleviating the symptoms of terminal cancers, and is therefore useful as a pain alleviation agent to relieve the pains of terminal cancer patients. The dosage of the medical composition is appropriately determined according to the age, type of disease, symptom or the like of the patient. The above dose (a dose corresponding to 1,250 to 5,000 mg of BCAA, taken or administered once, or 2 to 5 times a day) can be adopted.

C. Production of Oral or Enteral Composition

The composition of the present invention can be produced by a usual method.

For example, the processing of the composition of the present invention into a liquid, gel, or semisolid can be performed by a usual method. A specific example may be a process in which the measured amount of ingredients are added to water or hot water and sufficiently mixed; thereafter, the mixture is emulsified, packed in a pouch, and sterilized.

The processing of the composition of the present invention into a gel (jelly) can be performed by a usual method for producing a gel-type preparation. For example, the gel composition is produced by adding the measured amount of ingredients including a gelatinizer to water or hot water until the ingredients are dissolved or dispersed in water, well-mixing the solution or dispersion at a temperature greater than the temperature causing gelatinization, and then cooling the mixture to obtain a gel.

II. Treatments Using Oral or Enteral Composition, and Usages of Oral or Enteral Composition As mentioned above, the composition of the present invention is effective for the above-mentioned various usages.

Accordingly, the present invention further provides a method for recovery from fatigue; a method for suppressing lactic acid production in a living body; a method for improving the general states of valetudinarians or convalescing patients (particularly, elderly people and rehabilitants); a method for alleviating protein energy malnutrition (PEM) or cachexia in cancer patients; a method for alleviating biological invasion such as cancer treatments or cachexia in chronic obstructive lung disease (COPD); a method for alleviating or treating debilitating illness such as injury, infectious diseases or the like; a method for alleviating or treating cancers; and a method for alleviating various symptoms of terminal cancers. These methods are carried out by administering the above composition of the present invention to the object patient. The details of the composition, object patients, dosage etc. are the same as those in the above section "I. Oral or enteral composition".

The present invention further provides a use of the above composition for producing drug prepratrations for use in the various purposes, including recovery from fatigue; suppression of lactic acid production in a living body; improvement in the general states of valetudinarians or convalescing patients (particularly, elderly people and rehabilitants); alleviation of protein energy malnutrition (PEM) or cachexia in cancer patients; alleviation of biological invasion such as cancer treatment or cachexia in chronic obstructive lung disease (COPD); alleviation or treatment of debilitating illness such as injury, infectious diseases or the like; alleviation or treatment of cancers; and alleviation of various symptoms of terminal cancers. The details of the composition, dosage etc. in these usages are the same as those in the above section "I. Oral or enteral composition".

EXAMPLES

The present invention is more specifically explained below in reference to the following Examples. The present invention is, however, not limited to those examples.

Example 1

The components were measured according to the formulation of Table 1. 500 L of hot water at 85° C. was poured in a 1,000 L high-speed stirring tank. The components shown in Table 1 were added to the tank, and the components were repeatedly stirred to mix the components well. The temperature of the mixture liquid was kept at or higher than 70° C. To improve the solubility, maltodextrin was added before adding a gelatinizer.

Thereafter, the mixture was packed in a container and cooled at or below 40° C. A gel composition was obtained.

The viscosity of the gel composition was adjusted appropriately to a level suitable for a jelly product or a liquid food.

TABLE 1

| Ingredients (unit) | Materials | Example 1 |
|---|---|---|
| Protein (g) | Dry yeast | 1.8*1 |
| Carbohydrate (sugar) (g) | Sugar (maltodextrin) | 31.6 |
| Dietary fiber (g) | Enzymatically hydrolyzed guar gum | 1 |
| Water (g) | Purified water | Remainder |
| Gelatinizer (g) | Mixture of locust bean gum and carrageenan*2 | 1.26 |
| Perfume | Pineapple flavor | q.s. |
| BCAA (mg) | | 2500 |
| Valine | | (750) |
| Leucine | | (917) |
| Isoleucine | | (833) |
| $CoQ_{10}$ (mg) | Product of Nisshin Pharma Inc. | 30 |
| L-carnitine (mg) | | 50 |
| Citric acid (mg) | | 1000 |
| Mineral (mg) | | |
| Zinc | | 3.1 |
| Copper | | 0.31 |
| Calcium | | 147 |
| Vitamin | | |
| Vitamin $B_1$ (mg) | | 1.1 |
| Vitamin $B_2$ (mg) | | 3.0 |
| Vitamin $B_6$ (mg) | | 1.1 |
| Vitamin $B_{12}$ (μg) | | 1.5 |

TABLE 1-continued

| Ingredients (unit) | Materials | Example 1 |
|---|---|---|
| Vitamin E (mg) | | 10 |
| Total ingredients (g) | | 140 |

[1]The amount of protein is a value (g) obtained by multiplying the total amount of nitrogen atom contained in dry yeast in the composition and nitrogen atom contained in BCAA in the composition by 6.25.
[2]Mixture of "Neosoft JCC-M" and "Neosoft J-51" produced by Taiyo Kagaku Co. Ltd.

Table 2 shows the physical properties of the gel composition.

TABLE 2

| Physical Properties of gel composition | |
|---|---|
| Viscosity (mPa · s, 25° C.)* | 13000 |
| pH | 3.8 |
| Specific gravity | 1.1 |
| Calories (Kcal) per 140 g | 134 |
| Color | Transparent yellow |

*Viscosity is a value measured by a B-type rotation viscosity meter (RB-80L, Toki Sangyo Co. Ltd.) using a rotor M3, at 6 rpm and 25° C.

Test Example 1

A test was carried out to examine the effect of the gel composition prepared in Example 1 during exercise by orally administering the composition to healthy adult men and women.

(1) Test Method

Twenty healthy adult men and women (ten men and ten women) were selected as test subjects. They were told the objective of the test, and agreed to the test method. The test subjects were randomly classified into two groups: a gel composition administration group ("administration group", hereinafter) and a control group in which the administration of the composition was not performed. Each group consisted of five men and five women. The average age of the administration group was 27.4±3.8 years old, and the average age of the control group was 31±5.2 years old. There was no significant difference in age between the two groups.

The test was carried out by subjecting the two groups to a four-week exercise program (three times a week). During the test, somatometry values, athletic ability, feeling of fatigue, lactic acid value, etc. were measured for each test subject before the exercise program, two weeks after the beginning of the exercise program, and four weeks after the beginning of the exercise program. During the exercise program, the administration group took a 140 g dose of the gel composition prepared in Example 1 once or twice a day.

(2) Test Results
(a) Six-Minute Walking Test

TABLE 3

Changes in walking distance in six-minute walking test

| Groups | Before exercise program | After two weeks of exercise program | Unit: m After four weeks of exercise program |
|---|---|---|---|
| Administration group (10 people) | 618 ± 68.3 | 676.6 ± 82.4 | 736.9 ± 120.6 |
| Control group (10 people) | 608.2 ± 71.4 | 638.8 ± 79.9 | 708.6 ± 119.5 |

For the administration group, the walking distance in the six-minute walking test was 618±68.3 m before the program, 676.6±82.4 m after two weeks, and 736.9±120.6 m after four weeks. For the control group, the walking distance in the six-minute walking test was 608.2±71.4 m before the program, 638.8±79.7 m after two weeks, and 708.6±119.5 m after four weeks. There was no significant difference in the walking distance between the two groups.

(b) Lactic Acid Value

TABLE 4

Changes in lactic acid value

| Groups | Before exercise program | After two weeks of exercise program | Unit: mmol/l After four weeks of exercise program |
|---|---|---|---|
| Administration group (10 people) | 12.7 ± 6.4 | 7.8 ± 5.3 | 7.2 ± 4.0 |
| Control group (10 people) | 7.4 ± 3.2 | 7.2 ± 1.6 | 7.9 ± 3.2 |

For the administration group, the lactic acid value was 12.7±6.4 mmol/L before the program, 7.8±5.3 mmol/L after two weeks, and 7.2±4.0 mmol/L after four weeks. For the control group, the lactic acid value was 7.4±3.2 mmol/L before the program, 7.2±1.6 mmol/L after two weeks, and 7.9±3.2 mmol/L after four weeks. The decrease in lactic acid value was significant ($p<0.05$) in the administration group both after two weeks, and after four weeks.

(c) Feeling of Fatigue

Changes in the feeling of fatigue were evaluated according to VAS. VAS (visual analog scale) is a method of evaluating pain or feeling of fatigue based on a 10 cm straight line measure with scales. Level 0 indicates a state of no pain or feeling of fatigue, and Level 10 indicates a state of greatest pain or feeling of fatigue.

TABLE 5

Changes in feeling of fatigue (VAS)

| Groups | Before exercise program | After two weeks of exercise program | After four weeks of exercise program |
|---|---|---|---|
| Administration group (10 people) | 52.3 ± 18.7 | 51.8 ± 18.4 | 51.2 ± 21.5 |
| Control group (10 people) | 57.5 ± 14.0 | 67.9 ± 13.2 | 67.1 ± 16.4 |

For the administration group, the feeling of fatigue (VAS) was 52.3±18.7 before the program, 51.8±18.4 after two weeks, and 51.2±21.5 after four weeks. For the control group, the feeling of fatigue (VAS) was 57.5±14.0 before the program, 67.9±13.2 after two weeks, and 67.1±16.4 after four weeks. As such, the feeling of fatigue (VAS) was significantly low ($p<0.05$) after two weeks in the administration group.

(3) Observation and Results

In the both groups, the motile function was increased after a four-week exercise program.

However, the lactic acid value was greatly decreased in the administration group. Further, in the control group, the feeling of fatigue increased along with an increase in the walking distance. On the other hand, the administration group showed little change.

The results showed that administration of the composition of the present invention before or during the exercise is effective to inhibit lactic acid production or reduce feeling of fatigue.

Test Example 2

A test was carried out to examine the effect of the gel composition prepared in Example 1 during exercise by orally administering the composition to healthy elderly women.

(1) Test Method

Ten healthy elderly women (average age=68.8±3.8 years) were selected as test subjects. They were told the objective of the test, and agreed to the test method. The test subjects were randomly classified into two groups: a gel composition administration group ("administration group", hereinafter), and a control group in which the administration of the composition was not performed. Each group consisted of five women. The test was carried out by subjecting the two groups to a four-week muscle training and walking exercise (three times a week). The results obtained were based on their somatometry values and six-minute walking test. The lactic acid value was also measured after the six-minute walking test. During the test, the administration group took a 140 g dose of the gel composition prepared in Example 1 once or twice a day.

(2) Test Result (a) Six-Minute Walking Test

TABLE 6

Changes in walking distance in six-minute walking test

Unit: m

| Groups | Before exercise program | After four weeks of exercise program |
|---|---|---|
| Administration group (10 people) | 464 ± 88.5 | 548 ± 93.4 |
| Control group (10 people) | 460 ± 38.1 | 526 ± 42.2 |

For the administration group, the walking distance in the six-minute walking test was 464±88.5 m at the beginning of the test, and 548±93.4 m after four weeks. For the control group, the walking distance was 460±38.1 m at the beginning of the test, and 526±42.2 m after four weeks. The walking distance was increased in the administration group. The difference, however, was not significant.

(b) Changes in Lactic Acid Value

TABLE 7

Changes in lactic acid value

Unit: mmol/L

| Groups | Before exercise program | After four weeks of exercise program |
|---|---|---|
| Administration group (10 people) | 7.6 ± 1.3 | 3.2 ± 1.8 |
| Control group (10 people) | 5.7 ± 1.6 | 3.6 ± 1.0 |

For the administration group, the lactic acid value was 7.6±1.3 mmol/L at the beginning of the test, and 3.2±1.8 mmol/L after four weeks. For the control group, the lactic acid value was 5.7±1.6 mmol/L at the beginning of the test, and 3.6±1.0 mmol/L after four weeks. Accordingly, the administration group showed an apparent decrease in the lactic acid value, compared with the control group.

(c) Changes in Feeling of Fatigue

TABLE 8

Changes in feeling of fatigue (VAS)

| Groups | Before exercise program | After four weeks of exercise program |
|---|---|---|
| Administration group (10 people) | 75.8 ± 5.7 | 53.8 ± 10.5 |
| Control group (10 people) | 80.4 ± 2.6 | 70.8 ± 6.7 |

For the administration group, the evaluation of feeling of fatigue according to VAS was 75.8±5.7 at the beginning of the test, and 53.8±10.5 after four weeks. For the control group, the evaluation was 80.4±2.6 at the beginning of the test, and 70.8±6.7 after four weeks. Accordingly, in both groups, the feeling of fatigue was significantly decreased after four weeks compared with the feeling of fatigue at the beginning of the test. Between the two groups, the decrease was more significant in the administration group.

(3) Observation and Results

The results showed that the four-week exercise program increased the walking distance and decreased the lactic acid value in the administration group. In particular, the feeling of fatigue was significantly decreased in the administration group, showing a significant fatigue-reducing effect. The results showed that the administration of the composition of the present invention during exercise had a certain effect of facilitating improvement in motile function and recovery from fatigue, even for elderly people.

Test Example 3

Athletes who joined an eight-hour endurance motorbike race each took a 140 g dose of the gel composition prepared in Example 1 before the race and at each interval. Then, an increase in the lactic acid value as a fatigue stuff was evaluated.

The motorbikes ran at an average speed of 280 km/h, and the accompanying air resistance (wind pressure) caused the drivers considerable muscular exhaustion. Muscular exhaustion increases the lactic acid value, which is generally at least 4 mmol/L. Therefore, the athletes in such motorbike races always try to keep their lactic acid value at or below 4 mmol/L.

During the endurance race, the lactic acid value was measured at each interval. The values are shown in the following table.

TABLE 9

Changes in lactic acid value of drivers

| | Before race | First run | Second run | Third run | Fourth run |
|---|---|---|---|---|---|
| Average value (mmol/L) | 1.0 | 0.8 | 1.6 | 1.9 | 0.9 |
| Range* (mmol/L) | 0.0-2.4 | 0.0-2.9 | 0.0-2.6 | 0.0-2.8 | 0.0-2.4 |
| Number of test subject | 7 people | 7 people | 7 people | 7 people | 4 people |

*Range from smallest value to greatest value among the test subjects

The results showed that no athlete had a lactic acid value of more than 3 mmol/L. This shows a smooth energy metabolism even during severe exercise, confirming efficient energy production from lactic acid.

Considering the test results of Test Examples 1 to 3 totally, it is clear that the composition of the present invention has versatile effects for facilitating recovery of bodily function with respect to (a) rehabilitants (stroke patients, patients having digestion or deglutition difficulties), (b) early ambulation of elderly people, (c) patients under cancer treatments such as operations, chemotherapies, radial ray treatments, (d) patients convalescing from biological invasions such as cancer treatments, (e) patients having cachexia derived from advanced cancers, (f) fatigue from exercise, and (g) athletes.

According to the constitution of the composition of the present invention, the same effect can be given by other forms of the composition as long as they have the same constitution. For example, the composition of the present invention may be processed into drinks, granules, powders, or tablets.

Further, by processing the composition of the present invention into a gel (jelly) having a high viscosity, patients having difficulty in the deglutition of food or liquid due to diseases or aging can take the composition orally. Further, the high viscosity helps to prevent reverse flow when the composition of the present invention is administered through a tube via a gastric fistula; therefore, the composition of the present invention is useful for many people, including both healthy people and patients.

Test Example 4

The following experiment was carried out to analyze the effects, including the alleviation of symptoms, improvement in nutrition condition, antitumor effect, of the gel composition prepared in Example 1 with respect to terminal cancer patients (16 patients). The terminal cancer patients were those who had cancers that could not be treated by surgical operation, and that were untreatable by anticancer drugs.

The 16 patients with cancers were divided into a COBL group (gel composition administration group) and a control group. Each group consisted of eight patients. Their primary tumor sites were as follows.

COBL group: lung cancer (3 people), breast/uterine cancer (2 people), digestive cancer (3 people)

Control group: cranial nerve cancer (2 people), breast/uterine cancer (2 people), digestive cancer (3 people), kidney/urologic cancer (1 person)

Test Method 1 to 4 servings of thick fluid food (Ryflon QL (Nisshin Kyorin Pharmaceutical Co. Ltd.), Alginaid (Novartis Pharma K.K.) or HINE (Otsuka Pharmaceutical Factory Inc.) were supplied to the COBL group and the control group from 8 a.m. to 10 a.m., from 13:00 p.m. to 15:00 p.m., and from 17:00 p.m. to 19:00 p.m.

In the COBL group, 1 serving (140 g) of the gel composition prepared in Example 1 was supplied to each patient in the morning and during the day. Each patient took at least 1 serving a day.

At night, both the COBL group and the control group had hospital food and fluid infusion (BFLUID, Otsuka Pharmaceutical Factory Inc.) so that each patient had the necessary calories for a day.

The above administration was continued for four weeks.

With respect to algia, which is one of the evaluation items described above, during the administration, four people from the COBL group and three people from the control group were given various drugs when they complained of severe pain. The administration amount was 345±643 mg for the COBL group, and 203±503 mg for the control group, both based on morphine conversion. Four people from the COBL group and five people from the control group, who had pain but did not complain of severe pain, were not given the drugs. Under such conditions, the degree of algia alleviation effect of the gel composition was evaluated by the following evaluation method.

Evaluation Items

1) Clinical Symptoms

According to the evaluation criteria (face scale) shown in FIG. 7, the levels of algia, malaise, dyspnea, insomnia, and constipation were evaluated using a grading system. The overall evaluation, the sum of the scores of all symptoms, is shown in FIG. 1. The individual scores of the symptoms (algia, malaise, dyspnea, insomnia, and constipation) are shown in FIGS. 2 to 6. The values in the vertical axis in FIGS. 2 to 7 are average values, found by dividing the sum of the scores of all of the patients of the COBL group or the control group by 8. The values in the vertical axis in FIG. 1 are the sums of the averages of the scores of all symptoms.

2) Blood/Biochemical Inspection

A blood sample was collected from each patient on an empty stomach in the early morning so as to measure the lymphocyte concentration in the blood, the albumin concentration in the blood, the total protein concentration in the blood, and the serum lactic acid value. FIGS. 8 to 11 show the measurement results. The control group for the blood serum lactic acid value consisted of one person.

3) Antitumor Effect

A blood sample was collected from each patient on an empty stomach in the early morning so as to measure CRP (C-reactive protein). CRP is secreted in response to tissue degradation by cancer, and is known as a marker of tissue degradation. FIG. 12 shows the measurement results.

Results

FIGS. 1 to 12 indicate that the composition of the present invention is capable of alleviating the symptoms and improving the biochemical conditions of cancer patients. Further, FIG. 12 shows that the CRP in the COBL group dramatically decreased compared with the control group, thereby showing that the composition of the present invention can serve as an anticancer agent.

According to the results of Test Example 1, it is clear that the composition of the present invention provides, with respect to the cancer patients, efficient body energy production, prevents degradation of muscle protein while facilitating synthesis of muscle protein, and also provides an antitumor effect. In particular, the composition of the present invention has an excellent effect of alleviating the symptoms (algia, malaise, dyspnea, insomnia, and constipation) of terminal cancers, and is thereby effective to reduce pains of terminal cancer patient.

According to the constitution of the composition prepared in Example 1, the same effect can be given by other various forms as long as they have the same constitution. For example, the composition of the present invention may be processed into drinks, granules, powders, or tablets.

Further, by processing the composition of the present invention into a gel (jelly) having a high viscosity, patients having difficulty in the deglutition of food or liquid due to diseases or aging can take the composition orally. Further, the high viscosity helps to prevent reverse flow when the composition of the present invention is administered through a tube via a gastric fistula.

Test Example 5

The same experiment as in the above-mentioned Test Example 4 was performed with 16 additional terminal cancer patients. The 16 new patients were divided into a COBL group (gel composition administration group) and a control group. Each group consisted of eight patients. Their primary tumor sites were as follows.

COBL group: lung cancer (1 person), breast/uterine cancer (2 people), digestive cancer (3 people), kidney/urologic cancer (1 person)

Control group: lung cancer (1 person), digestive cancer (4 people), other cancer (3 people)

Test Method

The test method was the same as that of Test Example 4.

Examination Items and Results

The following test results show a summary of the test results of 16 terminal cancer patients subjected to the above-mentioned Test Example 4, and the additional 16 terminal cancer patients in the Test Example 5.

1) Clinical Symptoms

According to the evaluation criteria (face scale) shown in FIG. 13, the levels of algia, malaise, dyspnea, depression, anorexia, insomnia, nausea, constipation, and dry mouth were evaluated using a grading system. The overall evaluation, the sum of the scores of all symptoms, is shown in FIG. 14. The individual scores of the symptoms are shown in FIGS. 15 to 23. The values of the vertical axis in FIGS. 15 to 23 are average values, found by dividing the sum of the scores of all of the patients of the COBL group or the control group by 16. The values of the vertical axis in FIG. 14 are the sums of the averages of the scores of all symptoms.

2) Blood/Biochemical Inspection

A blood sample was collected from each patient on an empty stomach in the early morning so as to measure the lymphocyte concentration in the blood, the albumin concentration in the blood, the total protein concentration in the blood, and the serum lactic acid value. FIGS. 24 to 27 show the measurement results.

3) Antitumor Effect

A blood sample was collected from each patient on an empty stomach in the early morning so as to measure CRP (C-reactive protein). CRP is secreted in response to tissue degradation by cancer, and is known as a marker of tissue degradation. FIG. 28 shows the measurement results.

Results

As shown in FIGS. 24 to 28, the results of Test Example 5, which was performed with additional terminal cancer patients, were the same as those of Test Example 4. Accordingly, Test Example 5 also proved that the composition of the present invention had an anticancer effect, and is also capable of alleviating the pains of terminal cancer patients.

Test Example 6

The gel compositions (Examples 2-4) having the constituents shown in Table 10 were prepared using the same method as in Example 1.

TABLE 10

| Ingredients (unit) | Materials | Ex. 2 | Ex. 3 | Ex. 4 |
|---|---|---|---|---|
| Carbohydrate (sugar) (g) | Sugar (maltodextrin etc.) | 31.6 | 31.6 | 31.6 |
| Water (g) | Purified water | Remainder | Remainder | Remainder |
| Gelatinizer (g) | Mixture of locust bean gum and carrageenan*[1] | 1.26 | 1.26 | 1.26 |
| BCAA (mg) | | 2500 | 1120 | 7000 |
| Valine | | (750) | (336) | (2100) |
| Leucine | | (917) | (411) | (2568) |
| Isoleucine | | (833) | (373) | (2332) |
| $CoQ_{10}$ (mg) | Product of Nisshin Pharma Inc. | 30 | 14 | 98 |
| L-carnitine (mg) | | 50 | 7 | 420 |
| Citric acid (mg) | | 1000 | 112 | 2520 |
| Zinc (mg) | | 3.1 | 1.12 | 11.2 |
| Total ingredients (g) | | 140 | 140 | 140 |

*Ex. = Example
*[1]Mixture of "Neosoft JCC-M" and "Neosoft J-51" produced by Taiyo Kagaku Co. Ltd.

In the same manner as in Test Example 4, the effects of alleviating the symptoms, improving the nutritive conditions, and the antitumor effect of the gel composition (Example 2) with respect to terminal cancer patients were evaluated. In this test, the terminal cancer patients were divided into a COBL group (the gel composition administration group) and a control group as follows, with each group consisting of five patients.

COBL group: lung cancer (3 people), digestive cancer (2 people)

Control group: lung cancer (2 people), digestive cancer (2 people), kidney/urologic cancer (1 person)

As in Test Example 4, the results of this test showed that the COBL group (the group in which administration of the gel composition of the present invention was performed) had significant decrease in the symptoms (algia, malaise, dyspnea, insomnia, and constipation) of the terminal cancers compared with the control group. Further, in the COBL group (the group in which administration of the gel composition of the present invention was performed), it was observed that the biochemical conditions (results of blood/biochemical inspection) were improved, compared with the control group, with a dramatic decrease in CRP.

Moreover, the gel compositions of Example 3 and Example 4 were also separately administered to a terminal cancer patient (1 person) in the same manner as in Test Example 4, with the same results as above; i.e., they alleviated the symptoms of the terminal cancer, improved the biochemical conditions, and tended to decrease CRP.

Figure 1:
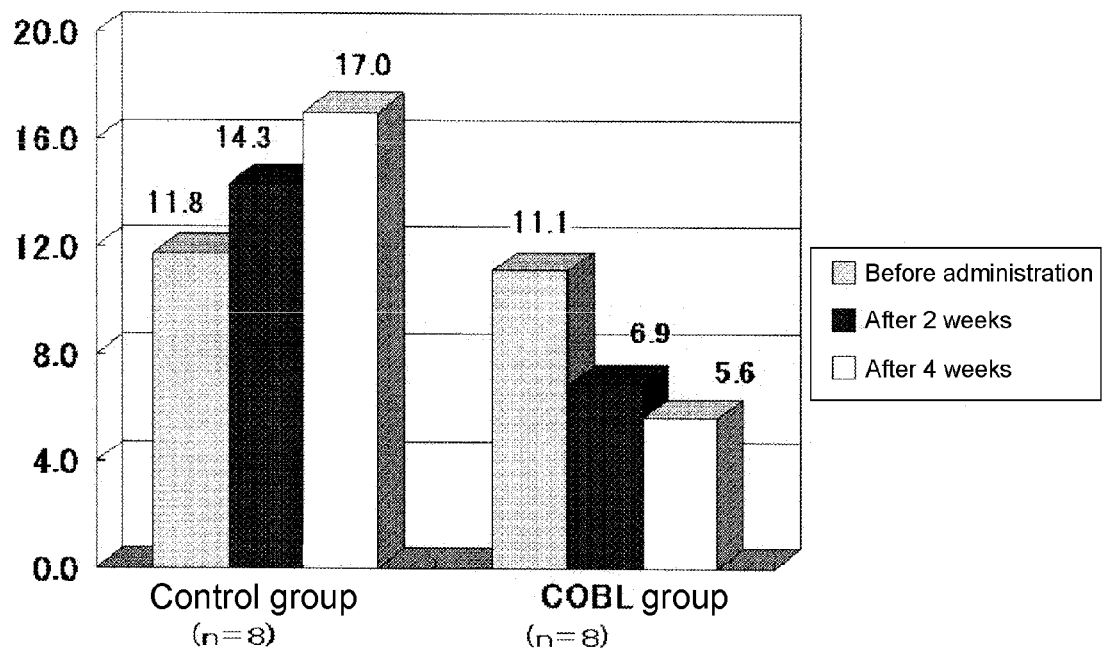
FIG. 1 is a graph showing an overall evaluation obtained by the sums of the clinical symptom evaluation in Test Example 4, based on the table in FIG. 7. The term "Before administration" in the figure represents the value at the time of hospitalization (this is the same for the other figures).
Figure 2:
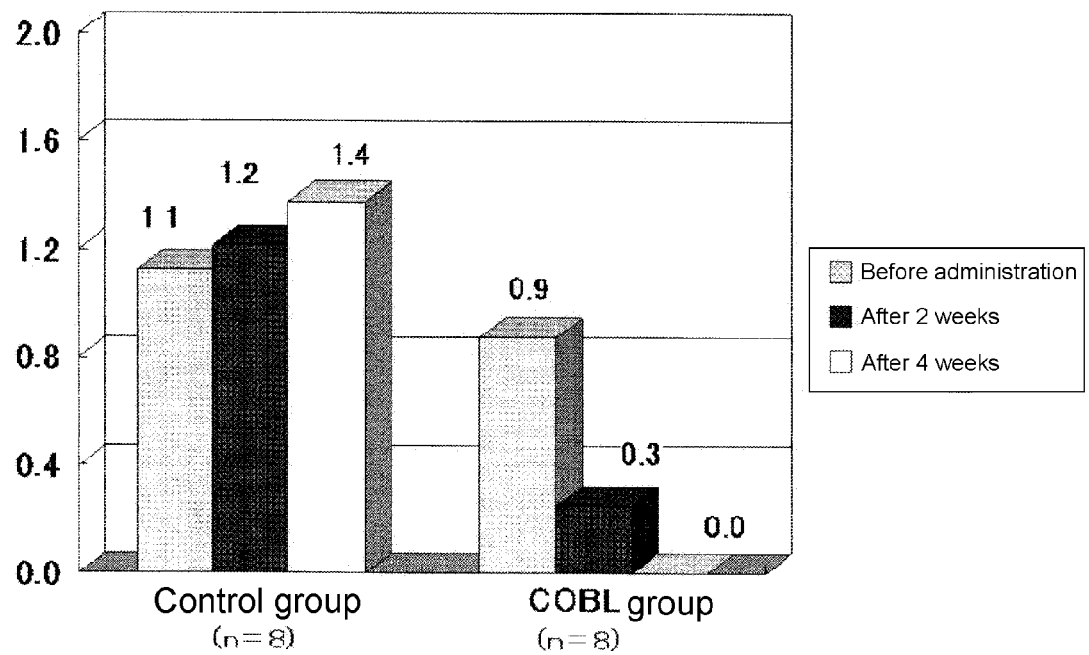
FIG. 2 is a graph showing an evaluation of algia, which is a symptom specified in FIG. 7, in Test Example 4.
Figure 3:
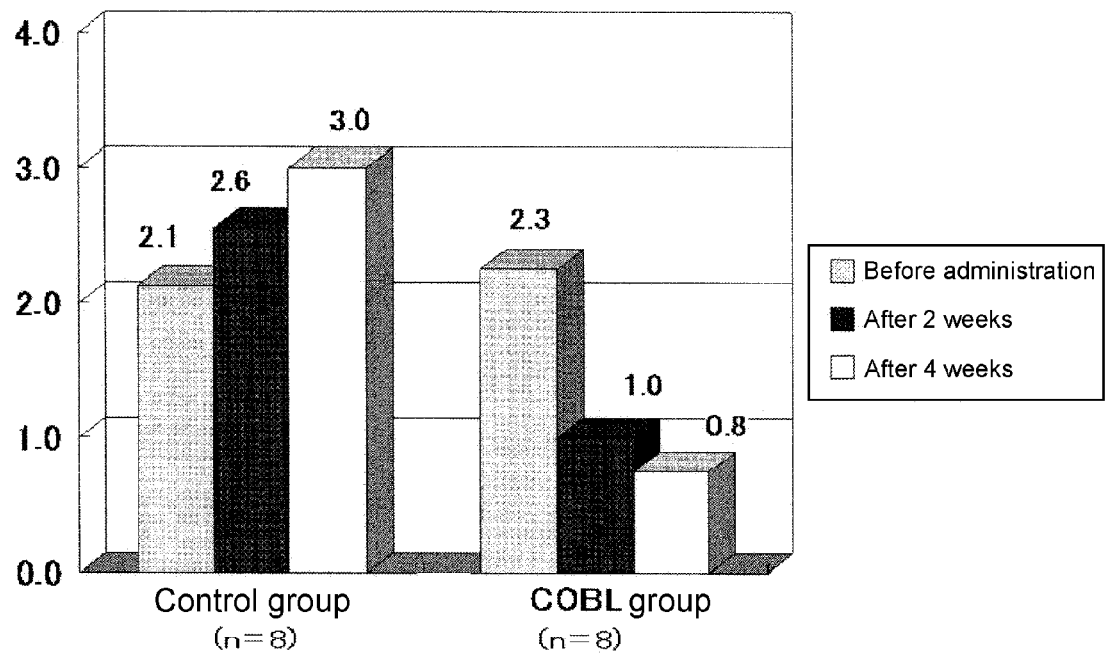
FIG. 3 is a graph showing an evaluation of malaise, which is a symptom specified in FIG. 7, in Test Example 4.
Figure 4:
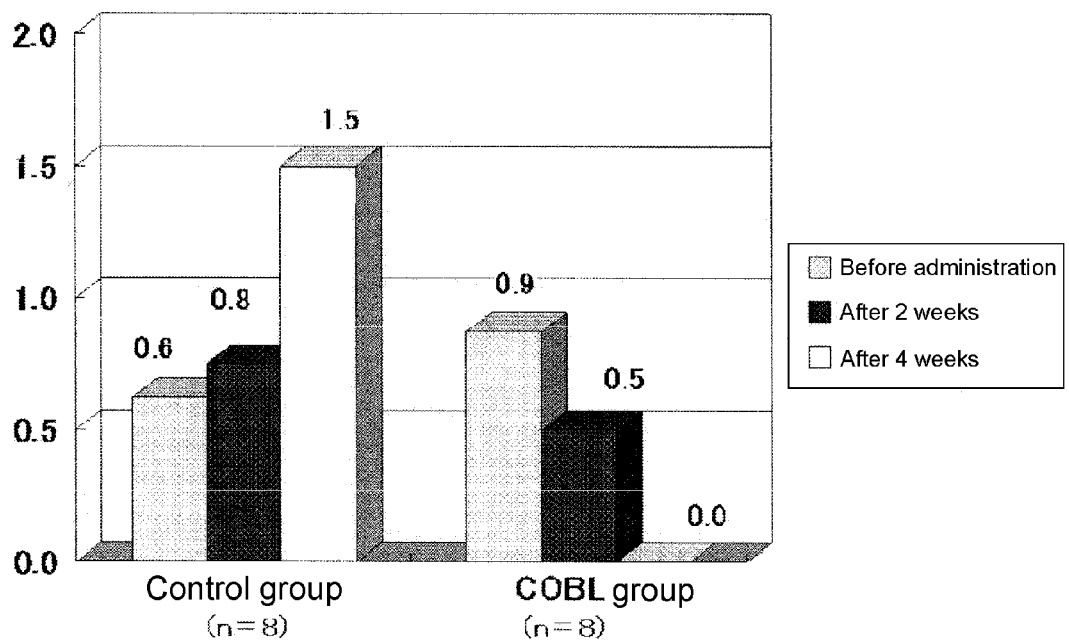
FIG. 4 is a graph showing an evaluation of dyspnea, which is a symptom specified in FIG. 7, in Test Example 4.
Figure 5:
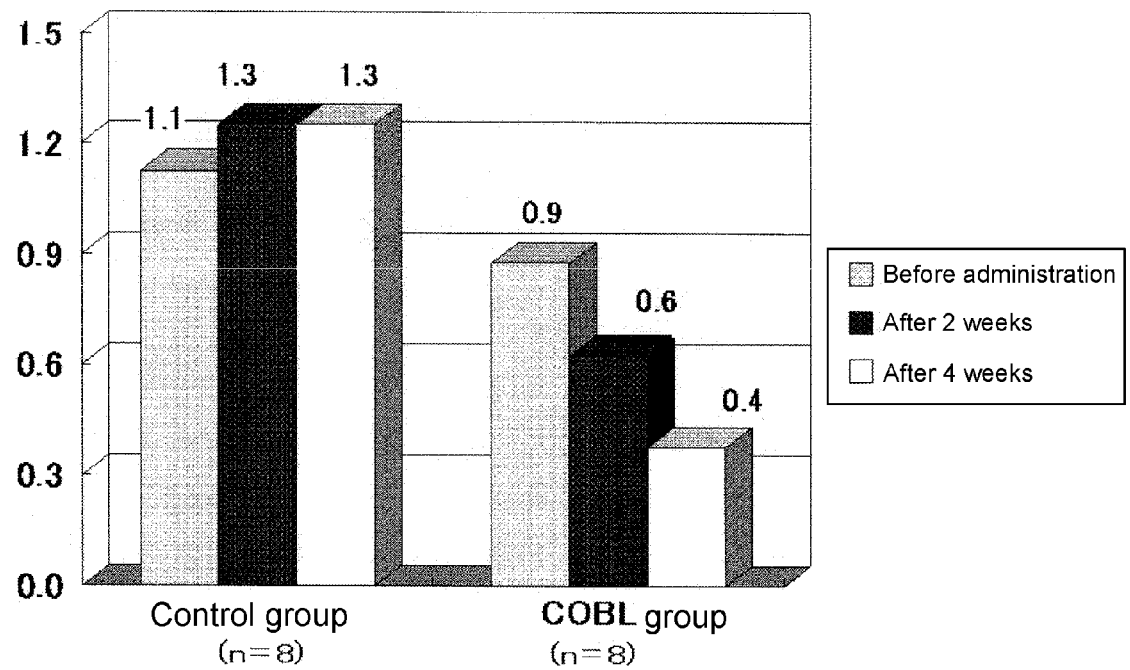
FIG. 5 is a graph showing an evaluation of insomnia, which is a symptom specified in FIG. 7, in Test Example 4.
Figure 6:
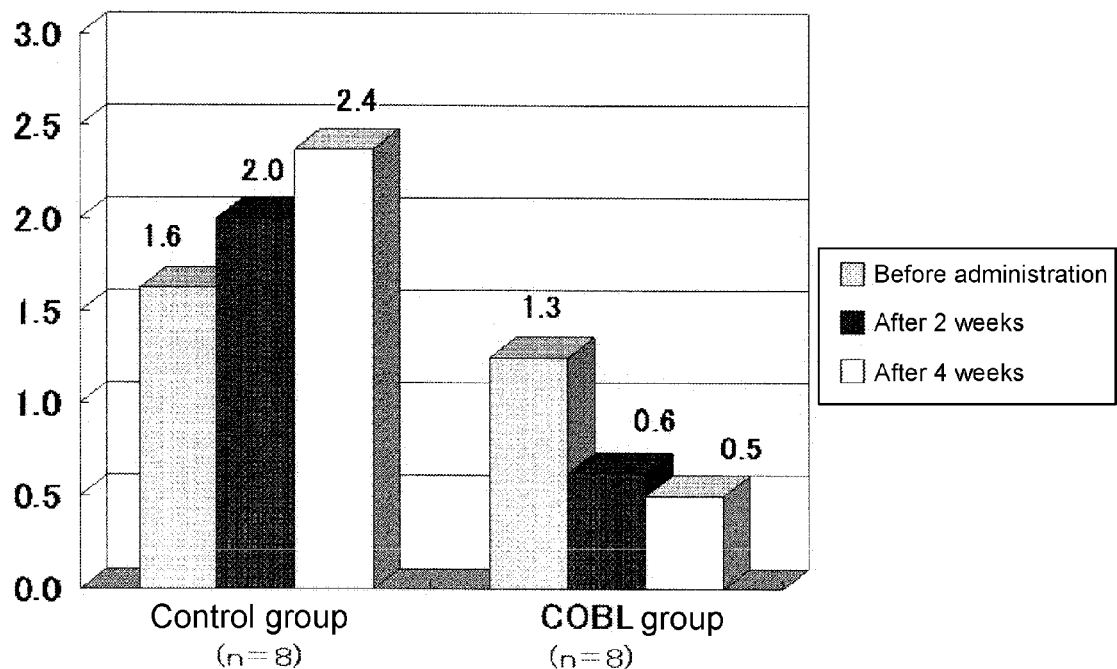
FIG. 6 is a graph showing an evaluation of constipation, which is a symptom specified in FIG. 7, in Test Example 4.
Figure 7:
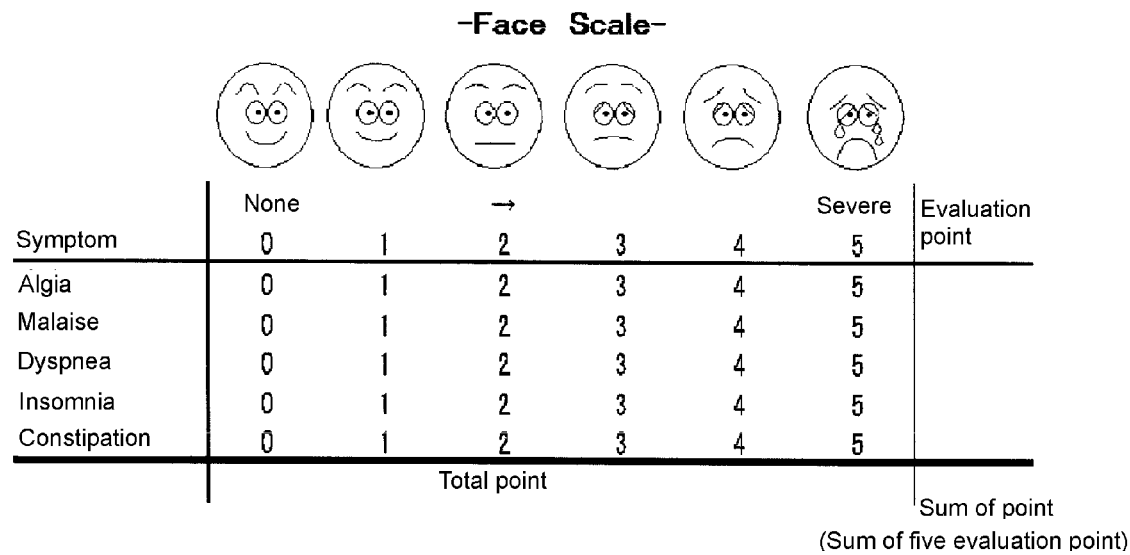
FIG. 7 is a table showing an overall evaluation obtained by the sums of the clinical symptom evaluation in Test Example 4.
Figure 8:
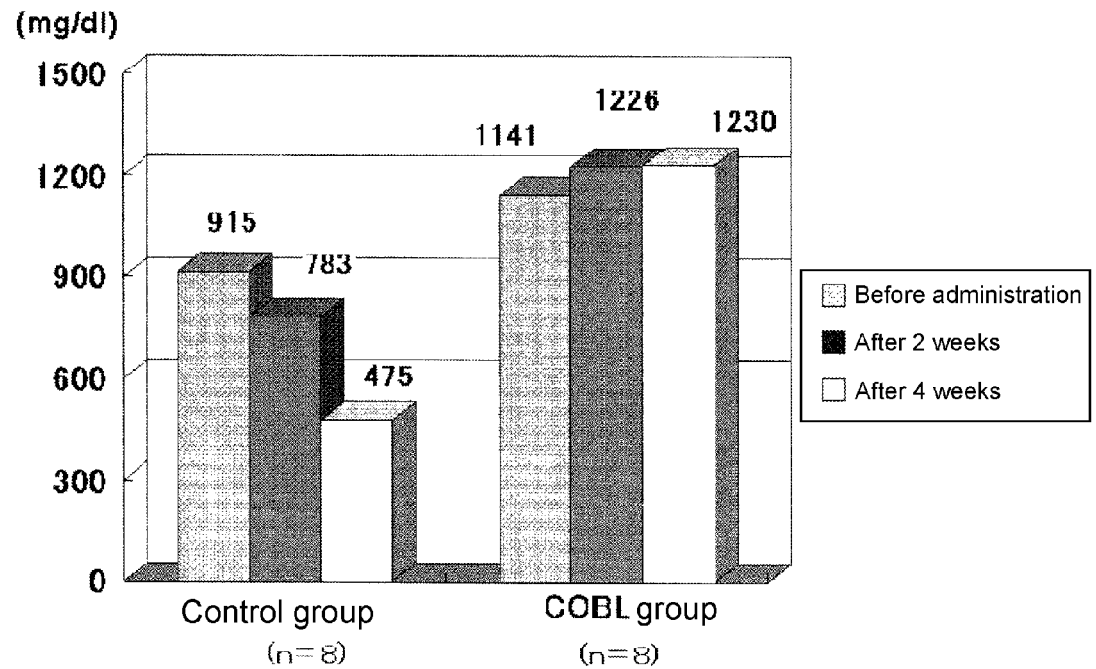
FIG. 8 is a graph showing an evaluation of lymphocyte concentration in the blood in Test Example 4.
Figure 9:
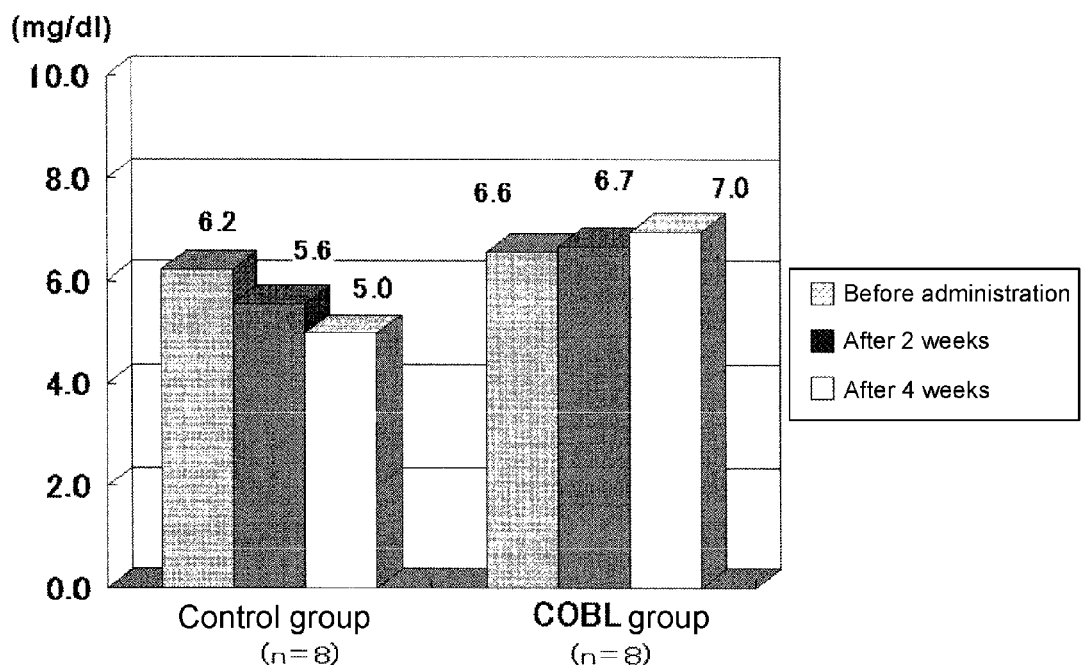
FIG. 9 is a graph showing an evaluation of total protein concentration in the blood in Test Example 4.
Figure 10:
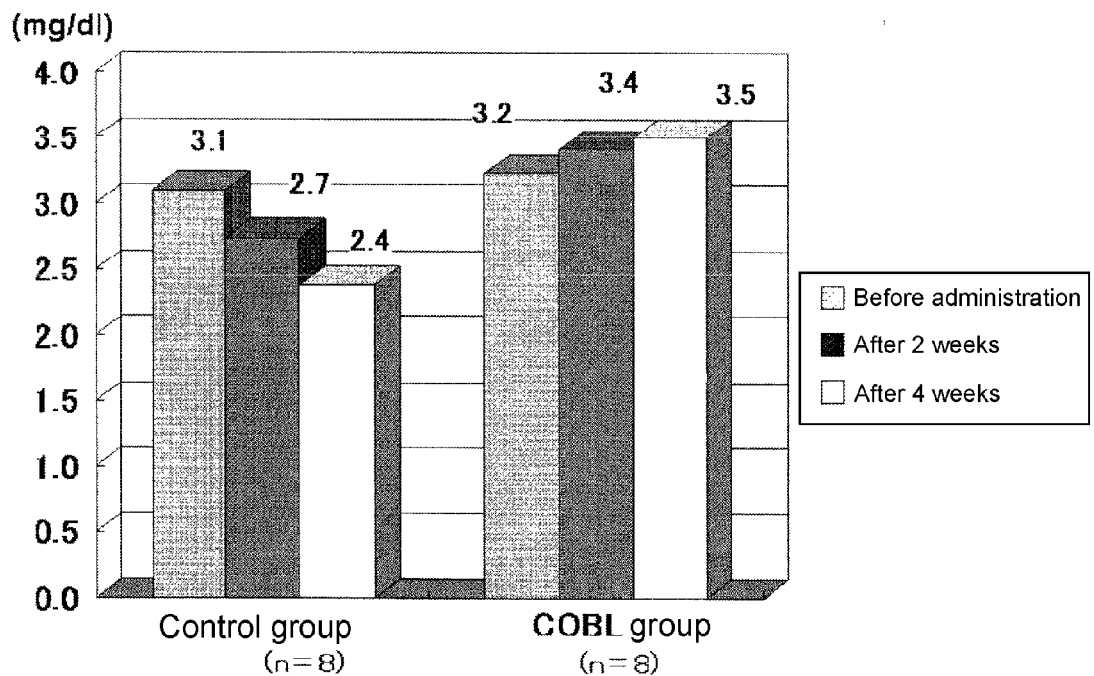
FIG. 10 is a graph showing an evaluation of albumin concentration in the blood in Test Example 4.
Figure 11:
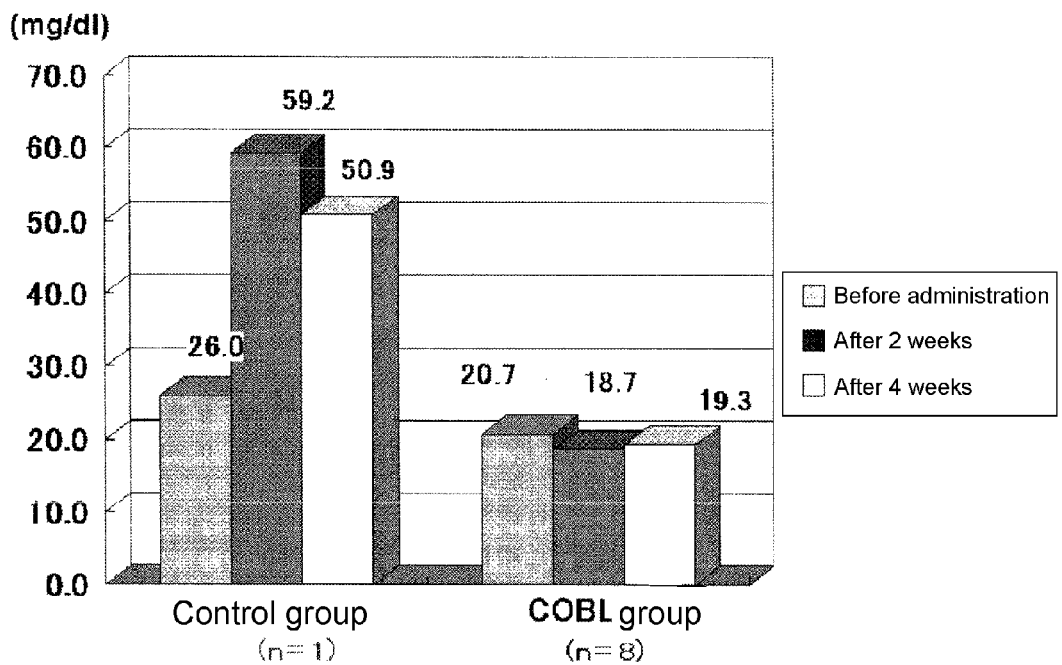
FIG. 11 is a graph showing an evaluation of blood serum lactic acid value in Test Example 4.
Figure 12:
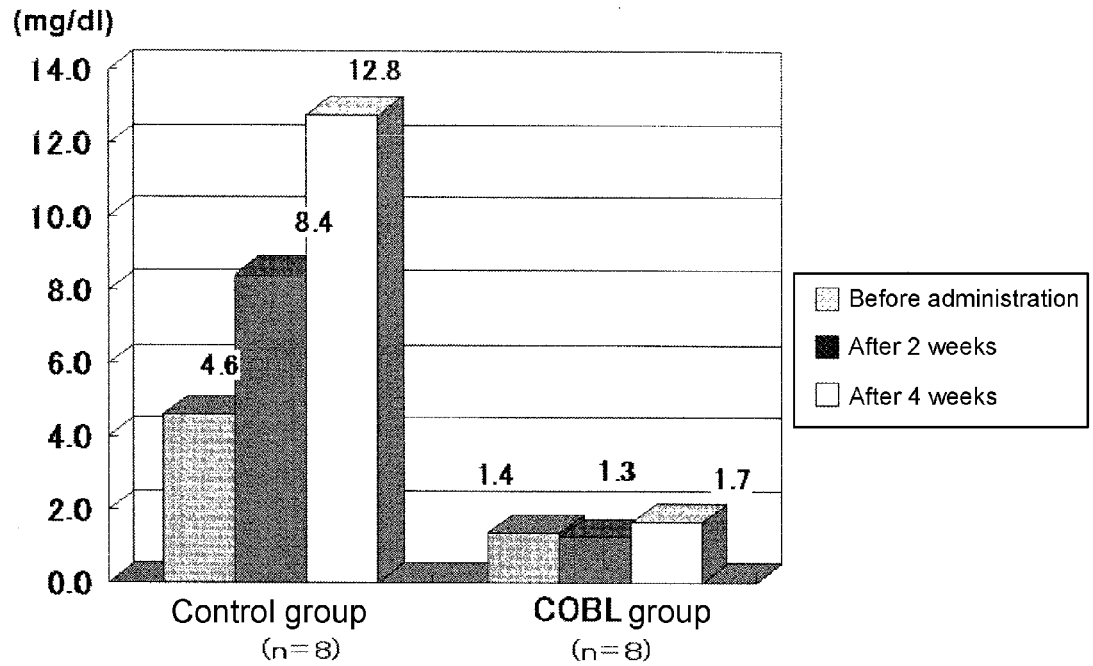
FIG. 12 is a graph showing an evaluation of CRP concentration in the blood in Test Example 4.
Figure 13:
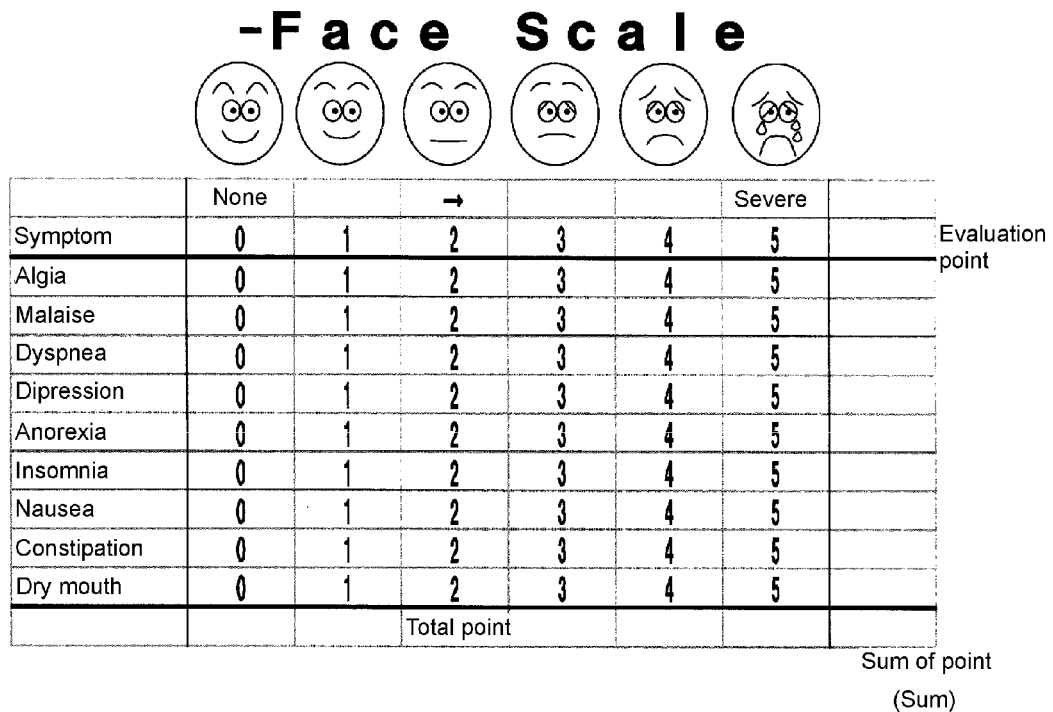
FIG. 13 is a table showing an overall evaluation obtained by the sums of the clinical symptom evaluation in Test Example 5.
Figure 14:
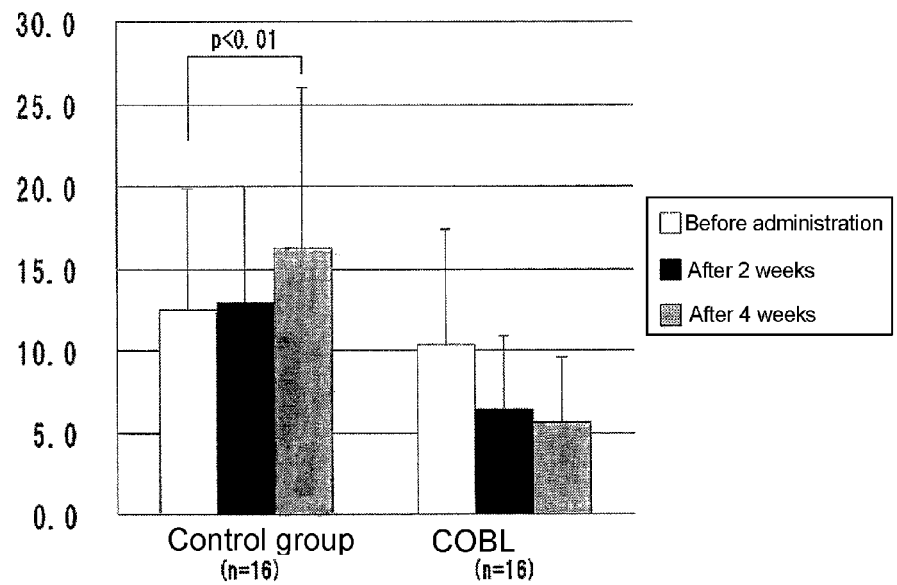
FIG. 14 is a graph showing an overall evaluation obtained by the sums of the clinical symptom evaluation in Test Example 5, based on the table in FIG. 13.
Figure 15:
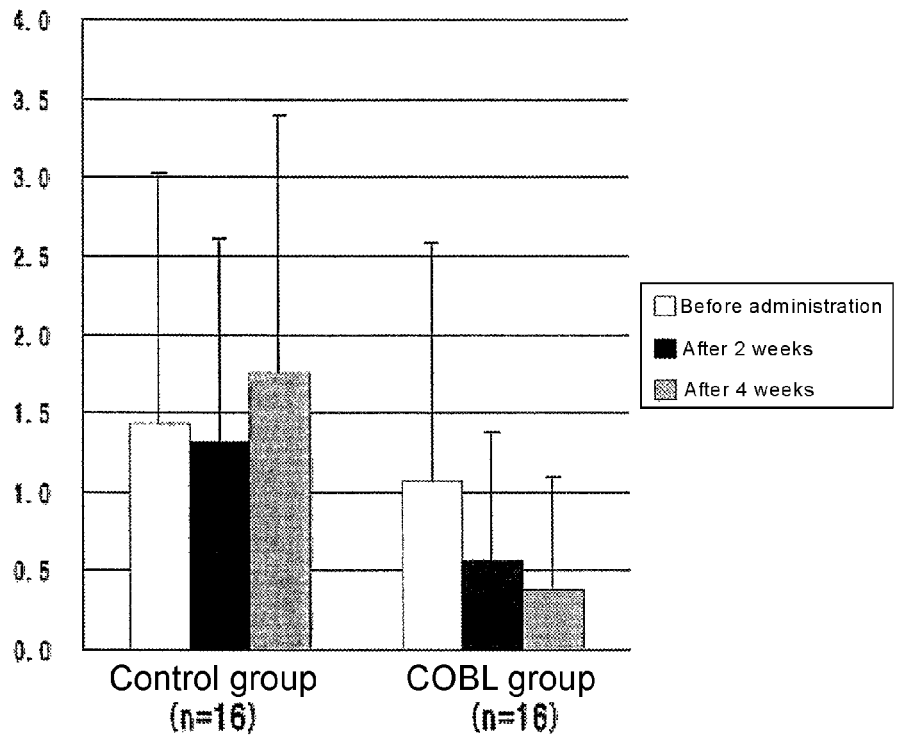
FIG. 15 is a graph showing an evaluation of algia, which is a symptom specified in FIG. 13, in Test Example 5.
Figure 16:
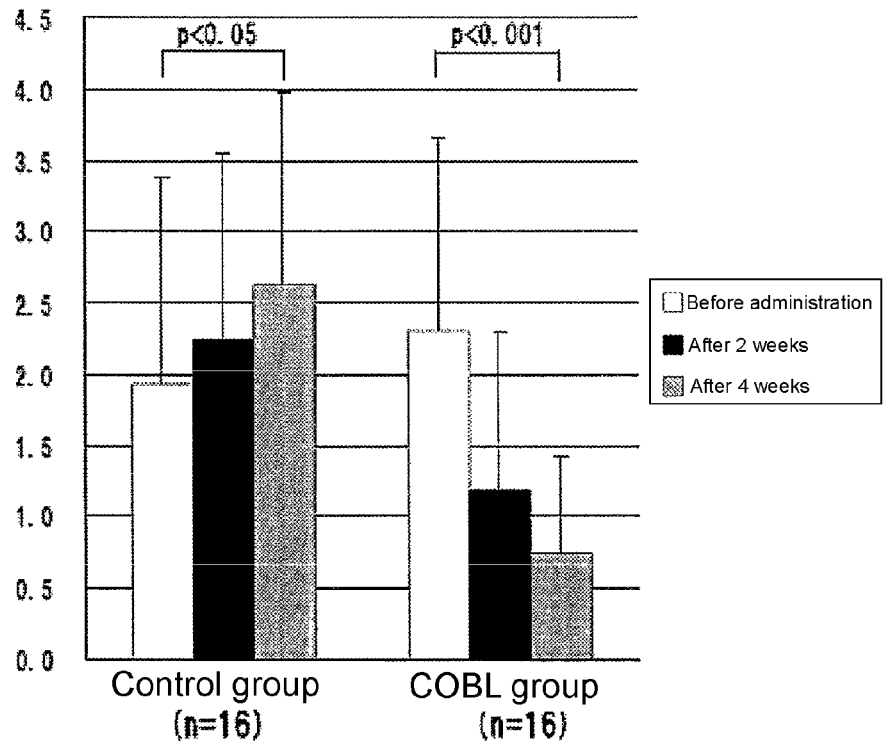
FIG. 16 is a graph showing an evaluation of malaise, which is a symptom specified in FIG. 13, in Test Example 5.
Figure 17:
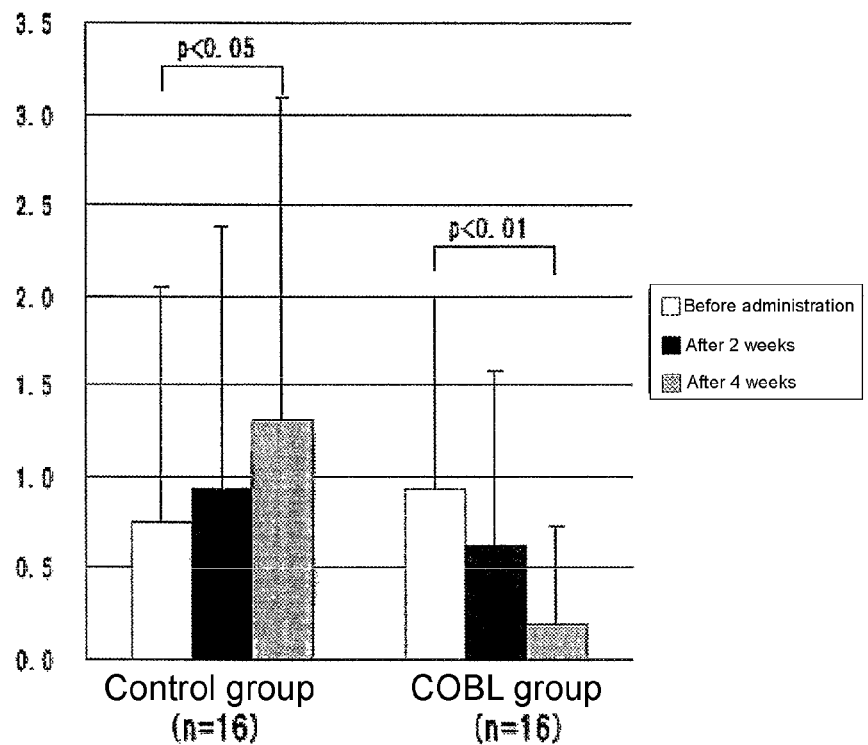
FIG. 17 is a graph showing an evaluation of dyspnea, which is a symptom specified in FIG. 13, in Test Example 5.
Figure 18:
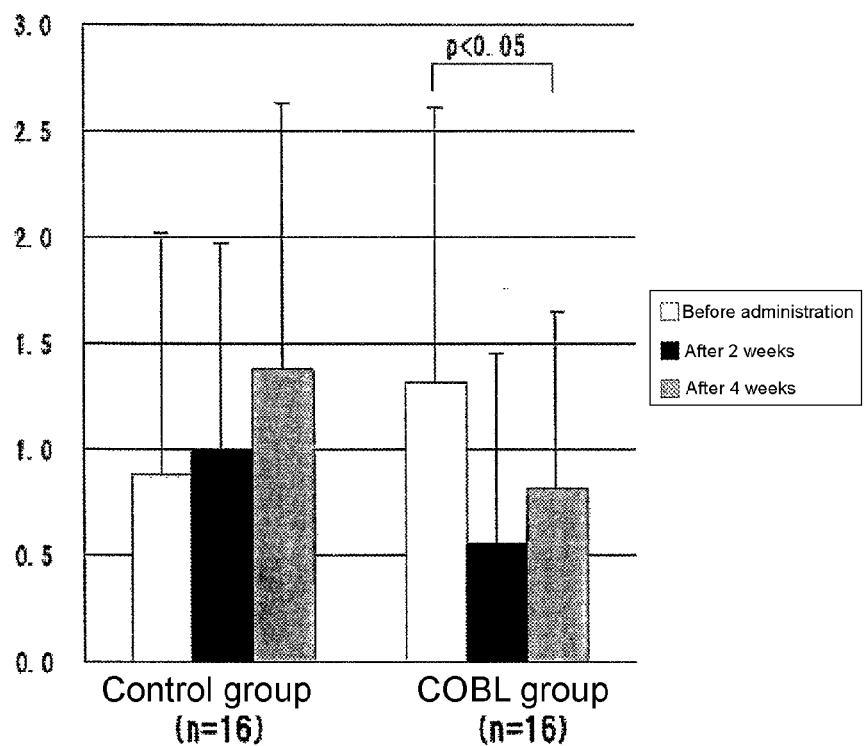
FIG. 18 is a graph showing an evaluation of depression, which is a symptom specified in FIG. 13, in Test Example 5.
Figure 19:
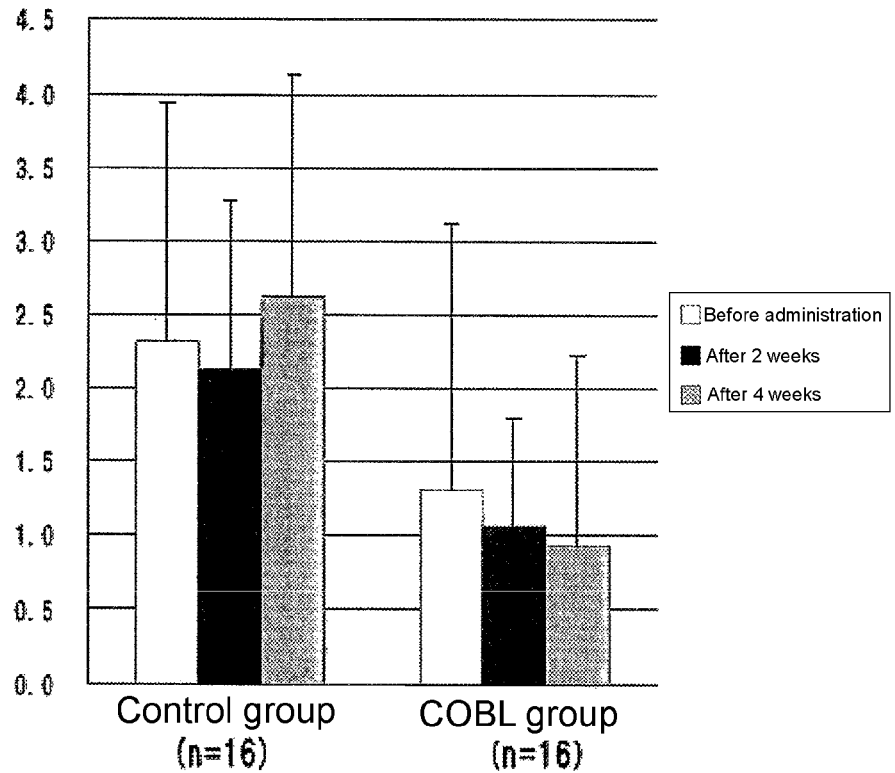
FIG. 19 is a graph showing an evaluation of anorexia, which is a symptom specified in FIG. 13, in Test Example 5.
Figure 20:
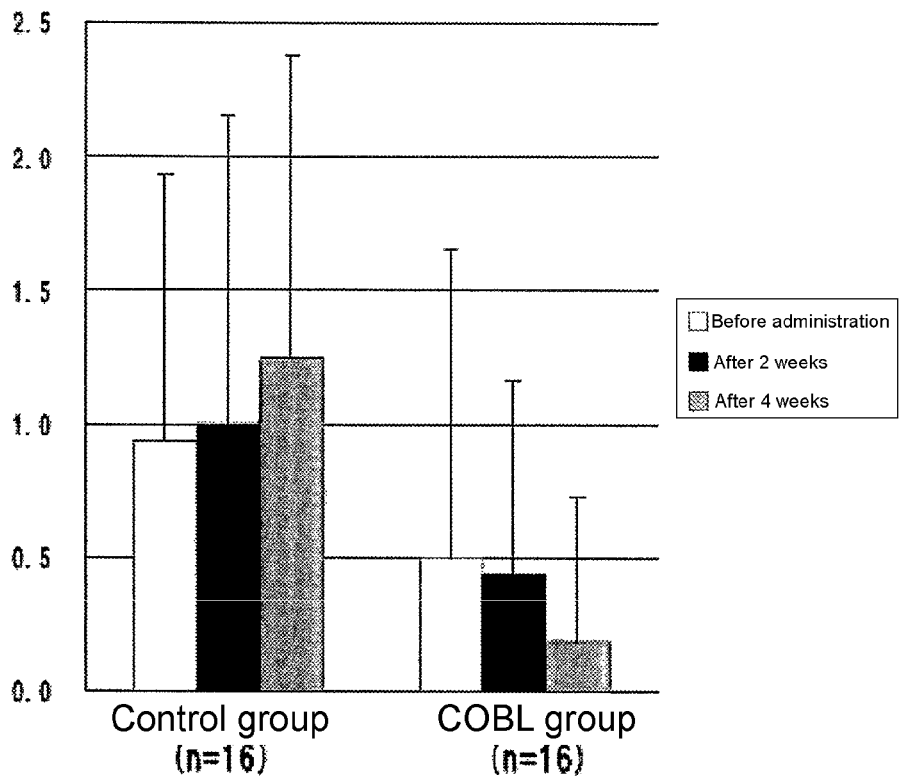
FIG. 20 is a graph showing an evaluation of insomnia, which is a symptom specified in FIG. 13, in Test Example 5.
Figure 21:
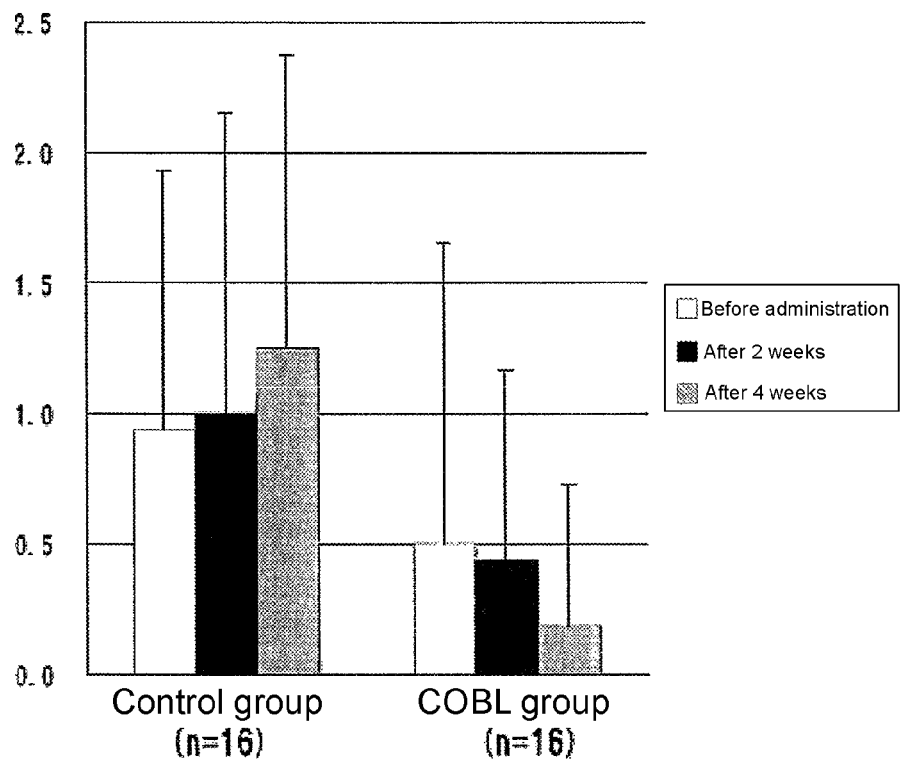
FIG. 21 is a graph showing an evaluation of nausea, which is a symptom specified in FIG. 13, in Test Example 5.
Figure 22:
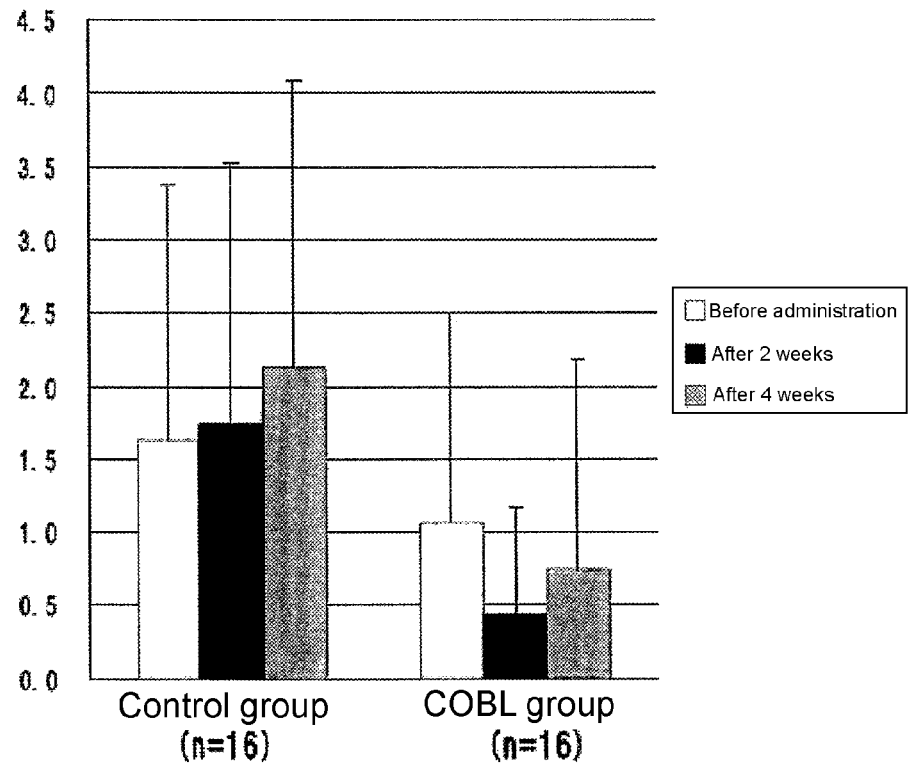
FIG. 22 is a graph showing an evaluation of constipation, which is a symptom specified in FIG. 13, in Test Example 5.
Figure 23:
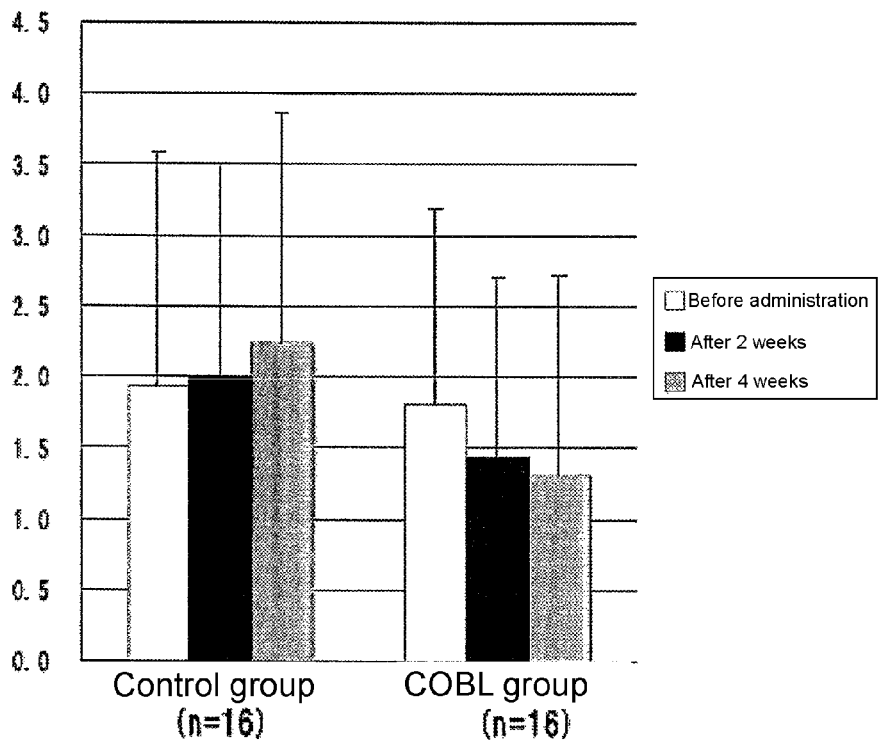
FIG. 23 is a graph showing an evaluation of dry mouth, which is a symptom specified in FIG. 13, in Test Example 5.
Figure 24:
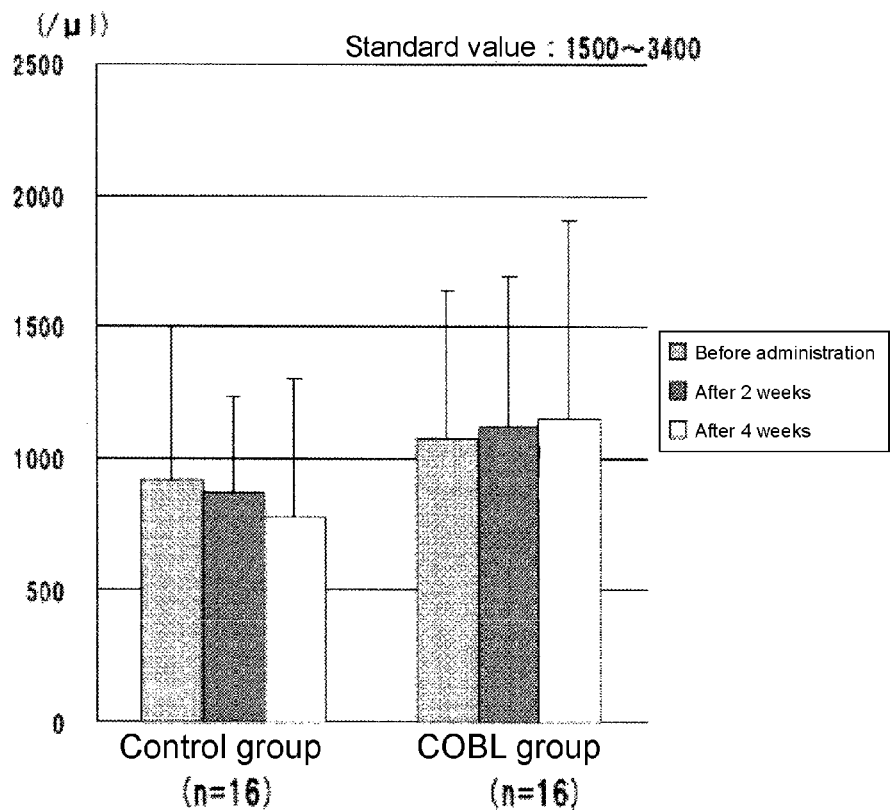
FIG. 24 is a graph showing an evaluation of lymphocyte concentration in the blood in Test Example 5.
Figure 25:
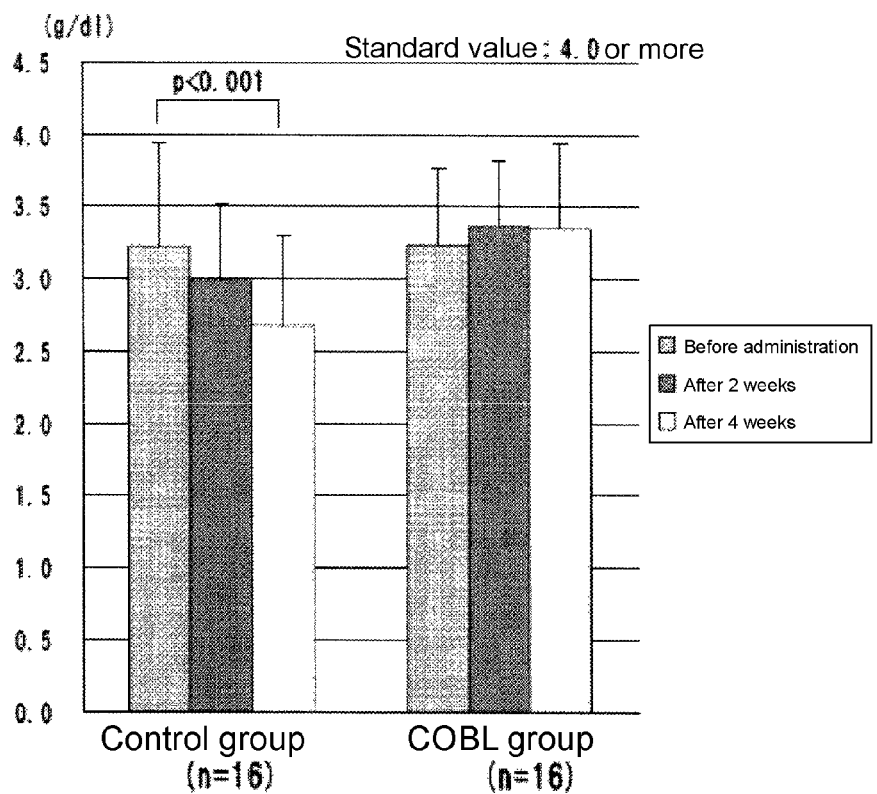
FIG. 25 is a graph showing an evaluation of albumin concentration in the blood in Test Example 5.
Figure 26:
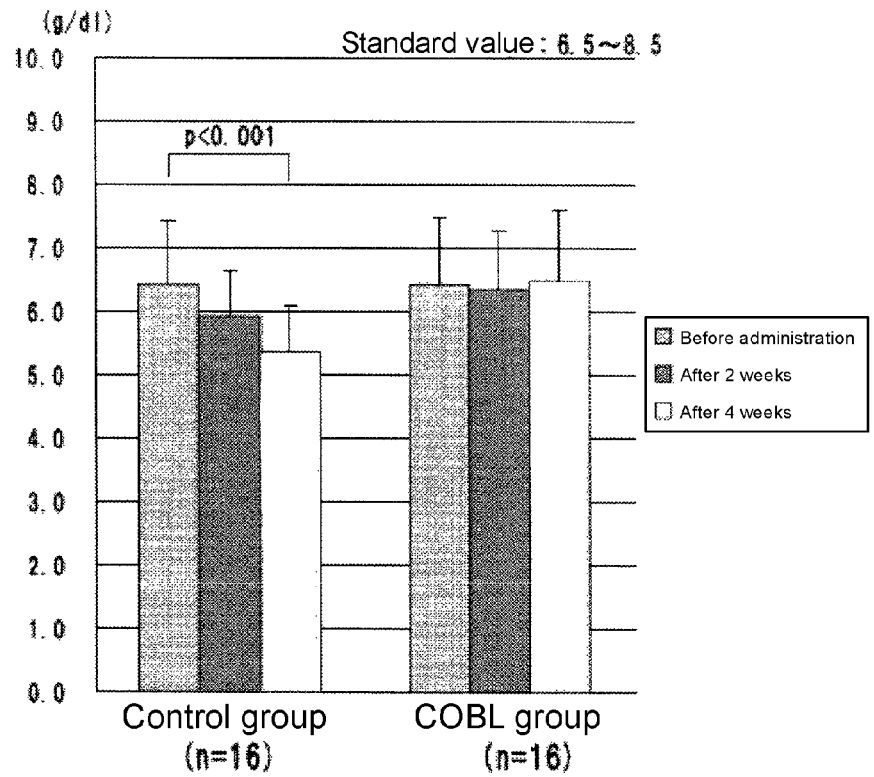
FIG. 26 is a graph showing an evaluation of total protein concentration in the blood in Test Example 5.
Figure 27:
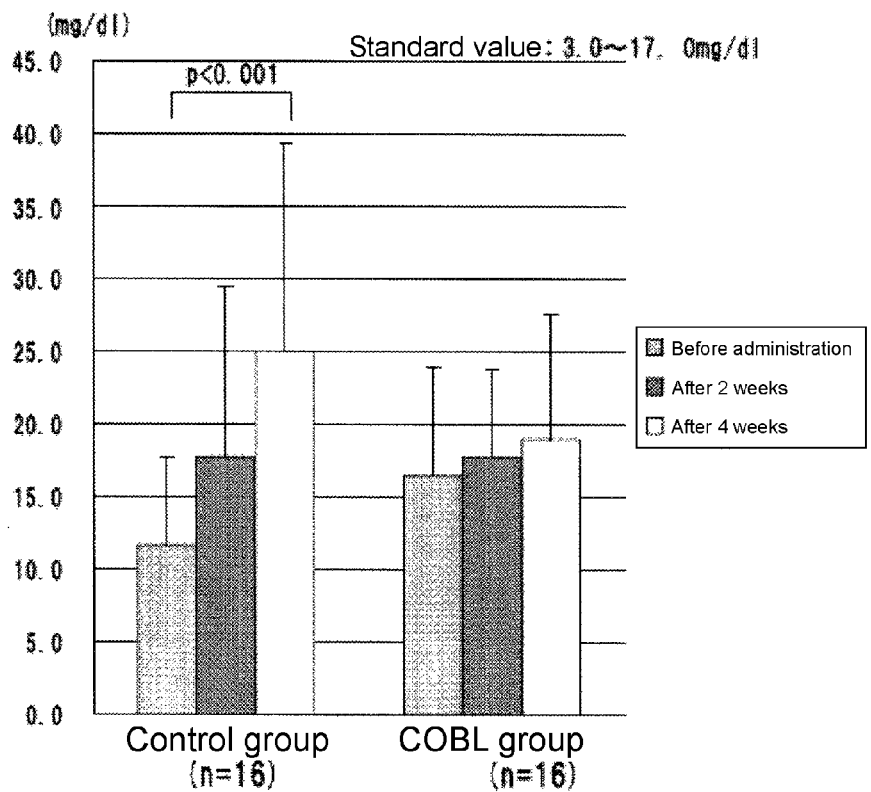
FIG. 27 is a graph showing an evaluation of blood serum lactic acid value in Test Example 5.
Figure 28:
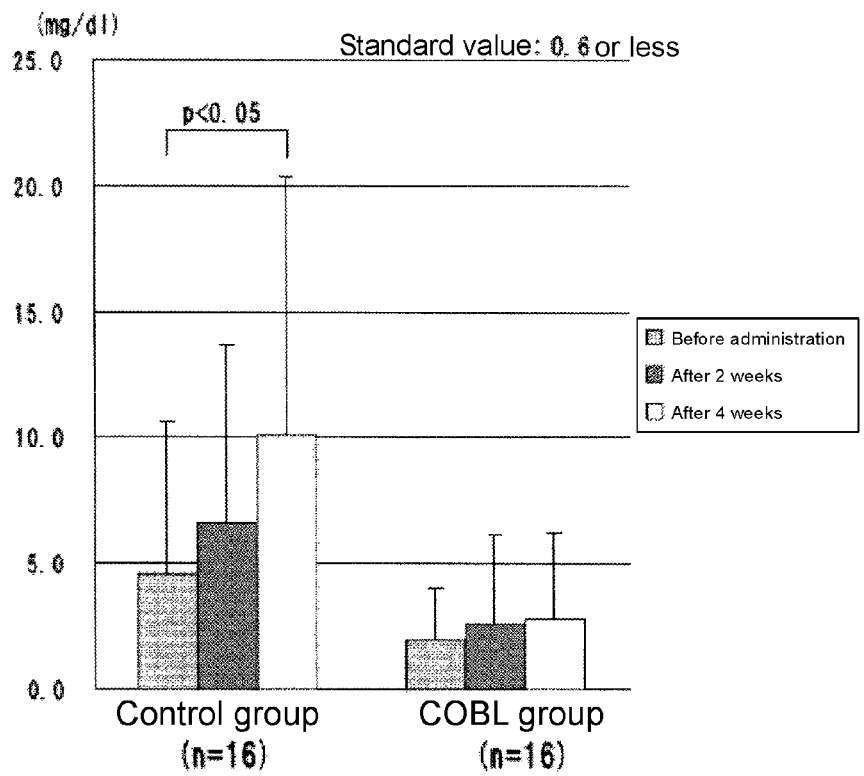
FIG. 28 is a graph showing an evaluation of CRP concentration in the blood in Test Example 5.

The invention claimed is:

1. An oral or enteral composition, comprising:
 a branched-chain amino acid,
 coenzyme $Q_{10}$,
 L-carnitine,
 citric acid, at least one gelatinizer, and
 zinc,
 wherein all gelatinizers contained in the oral or enteral composition are polysaccharides selected from the group consisting of gellan gum, pectin, curdlan, pullulan, locust bean gum, carrageenan, xanthan gum, guar gum, carboxymethylcellulose sodium, hydroxyethylcellulose, sodium alginate, agar, gum arabic and tragacanth, and
 wherein the oral or enteral composition comprises 1.0 to 3.0 wt. % of a branched-chain amino acid, 0.015 to 0.05 wt. % of coenzyme $Q_{10}$, 0.01 to 0.07 wt. % of L-carnitine, 0.1 to 1.5 wt. % of citric acid, and 0.001 to 0.0035 wt. % of zinc, based on the total amount of the composition, a ratio of the L-carnitine being 1.8 to 5 parts by weight, per 100 parts by weight of the branched-chain amino acid, and a ratio of the citric acid being 30 to 50 parts by weight, per 100 parts by weight of the branched-chain amino acid.

2. The oral or enteral composition according to claim 1, wherein the composition comprises 1.5 to 2.5 wt. % of a branched-chain amino acid, 0.018 to 0.03 wt. % of coenzyme $Q_{10}$, 0.03 to 0.05 wt. % of L-carnitine, 0.6 to 1.0 wt. % of citric acid, and 0.002 to 0.0028 wt. % of zinc, based on the entire amount of the composition.

3. The oral or enteral composition according to claim 1, wherein the branched-chain amino acid comprises valine, leucine and isoleucine at a weight ratio of 1:0.8 to 2.5:0.7 to 2.2.

4. The oral or enteral composition according to claim 1, wherein the oral or enteral composition further comprises 8 to 12 parts by weight of copper, per 100 parts by weight of zinc.

5. The oral or enteral composition according to claim 1, wherein the oral or enteral composition is a nutrient.

6. The oral or enteral composition according to claim 5, wherein the oral or enteral composition is a food for a cancer patient.

7. The oral or enteral composition according to claim 5, wherein the oral or enteral composition is a food for alleviating a symptom or improving nutritive condition of a cancer patient.

8. The oral or enteral composition according to claim 7, wherein the cancer patient is a terminal cancer patient.

9. The oral or enteral composition according to claim 1, wherein the oral or enteral composition is a pharmaceutical composition.

10. The oral or enteral composition according to claim 9, wherein the oral or enteral composition or enteral composition is used for treating cancers.

11. The oral or enteral composition according to claim 10, wherein the oral or enteral composition is used for treating terminal cancers.

12. The oral or enteral composition according to claim 1, wherein the oral or enteral composition is used for alleviating a symptom of terminal cancer.

13. The oral or enteral composition according to claim 12, wherein the symptom of terminal cancer is at least one selected from the group consisting of algia, malaise, dyspnea, insomnia, and constipation.

14. The oral or enteral composition according to claim 1, wherein the oral or enteral composition further comprises a mineral selected from the group consisting of copper, iron, sodium, potassium, phosphorus, and magnesium.

15. A method for treating a cancer, comprising:
 administering an oral or enteral composition to a cancer patient, the oral or enteral composition comprising
 a branched-chain amino acid,
 coenzyme $Q_{10}$,
 L-carnitine,
 citric acid, at least one gelatinizer, and
 zinc,
 wherein all gelatinizers contained in the oral or enteral composition are polysaccharides selected from the group consisting of gellan gum, pectin, curdlan, pullulan, locust bean gum, carrageenan, xanthan gum, guar gum, carboxymethylcellulose sodium, hydroxyethylcellulose, sodium alginate, agar, gum arabic and tragacanth, and
 wherein the oral or enteral composition comprises 1.0 to 3.0 wt. % of a branched-chain amino acid, 0.015 to 0.05 wt. % of coenzyme $Q_{10}$, 0.01 to 0.07 wt. % of L-carnitine, 0.1 to 1.5 wt. % of citric acid, and 0.001 to 0.0035 wt. % of zinc, based on the total amount of the composition, a ratio of the L-carnitine being 1.8 to 5 parts by weight, per 100 parts by weight of the branched-chain amino acid, and a ratio of the citric acid being 30 to 50 parts by weight, per 100 parts by weight of the branched-chain amino acid.

16. A method for alleviating a symptom of cancer, comprising:
administering an oral or enteral composition to a cancer patient, the oral or enteral composition comprising
a branched-chain amino acid,
coenzyme $Q_{10}$,
L-carnitine,
citric acid, at least one gelatinizer, and
zinc,
wherein all gelatinizers contained in the oral or enteral composition are polysaccharides selected from the group consisting of gellan gum, pectin, curdlan, pullulan, locust bean gum, carrageenan, xanthan gum, guar gum, carboxymethylcellulose sodium, hydroxyethylcellulose, sodium alginate, agar, gum arabic and tragacanth, and
wherein the oral or enteral composition comprises 1.0 to 3.0 wt. % of a branched-chain amino acid, 0.015 to 0.05 wt. % of coenzyme $Q_{10}$, 0.01 to 0.07 wt. % of L-carnitine, 0.1 to 1.5 wt. % of citric acid, and 0.001 to 0.0035 wt. % of zinc, based on the total amount of the composition, a ratio of the L-carnitine being 1.8 to 5 parts by weight, per 100 parts by weight of the branched-chain amino acid, and a ratio of the citric acid being 30 to 50 parts by weight, per 100 parts by weight of the branched-chain amino acid.

17. The method for alleviating a symptom of cancer according to claim 16, wherein the symptom of cancer is at least one selected from the group consisting of algia, malaise, dyspnea, insomnia, and constipation.

18. The method for alleviating a symptom of cancer according to claim 16, wherein the cancer is a terminal cancer.

* * * * *